(12) United States Patent
Maunder

(10) Patent No.: US 12,196,349 B2
(45) Date of Patent: Jan. 14, 2025

(54) CONNECTION SYSTEM

(71) Applicant: Bio Optimal Limited, Fareham (GB)

(72) Inventor: Roy Peter Maunder, Fareham (GB)

(73) Assignee: Bio Optimal Limited, Fareham (GB)

( * ) Notice: Subject to any disclaimer, the term of this patent is extended or adjusted under 35 U.S.C. 154(b) by 174 days.

(21) Appl. No.: 17/438,426

(22) PCT Filed: Mar. 11, 2020

(86) PCT No.: PCT/EP2020/056550
§ 371 (c)(1),
(2) Date: Sep. 11, 2021

(87) PCT Pub. No.: WO2020/182906
PCT Pub. Date: Sep. 17, 2020

(65) Prior Publication Data
US 2022/0146023 A1    May 12, 2022

(30) Foreign Application Priority Data
Mar. 12, 2019    (GB) ....................... 1903367

(51) Int. Cl.
*F16L 23/16* (2006.01)
*F16L 31/02* (2006.01)

(52) U.S. Cl.
CPC ............. *F16L 23/162* (2013.01); *F16L 31/02* (2013.01)

(58) Field of Classification Search
CPC ......... F16L 23/162; F16L 31/02; A61M 39/12
See application file for complete search history.

(56) References Cited

U.S. PATENT DOCUMENTS

| | | | |
|---|---|---|---|
| 3,099,015 A | 7/1963 | Renehan | |
| 3,380,764 A * | 4/1968 | Wilson | .................. F16L 33/224 285/903 |
| 3,563,573 A | 2/1971 | Crompton et al. | |
| 4,133,565 A | 1/1979 | Shutt | |
| 4,632,435 A | 12/1986 | Polyak | |

(Continued)

FOREIGN PATENT DOCUMENTS

| | | |
|---|---|---|
| CN | 208397501 U | 1/2019 |
| EP | 1130304 A2 | 9/2001 |

(Continued)

OTHER PUBLICATIONS

IPI, Examination Report for IN 202127043878, pp. 4 (mailed Apr. 17, 2023).

(Continued)

*Primary Examiner* — James M Hewitt, II
(74) *Attorney, Agent, or Firm* — UltimatEdge IP Law Group, P.C.; Dean G. Stathakis

(57) ABSTRACT

A system of connecting two flexible tubes together using rolled back ends of the tubes to create abutment surfaces which when urged together form a fluid-tight seal. The rolled back ends are supported on tube supports including a spigot extending along the outside of the tube and over which the rolled ends are supported. Urging two rolled backed ends together creates a fluid tight seal. In one example, this urging may be achieved by attaching flanges to the rolled back ends and using standard clamping methods. Alternatively, other types of clamping methods can be used.

18 Claims, 11 Drawing Sheets

(56) References Cited

U.S. PATENT DOCUMENTS

| | | | |
|---|---|---|---|
| 5,439,259 A * | 8/1995 | Taga | F16L 47/041 |
| | | | 285/334.5 |
| 5,791,696 A * | 8/1998 | Miyajima | F16L 33/01 |
| | | | 285/222.1 |
| 6,179,348 B1 | 1/2001 | Okamoto | |
| 6,354,636 B2 * | 3/2002 | Matsuzawa | F16L 23/08 |
| | | | 285/365 |
| 10,473,244 B2 * | 11/2019 | Nallet | F16L 19/025 |
| 2004/0035426 A1 | 2/2004 | Curran et al. | |
| 2012/0267891 A1 * | 10/2012 | Walz | B01D 46/02 |
| | | | 285/305 |

FOREIGN PATENT DOCUMENTS

| | | |
|---|---|---|
| JP | 60104314 A | 6/1985 |
| JP | 4224926 A | 8/1992 |
| JP | 2007048582 A | 2/2007 |
| WO | 2002035133 A1 | 5/2002 |
| WO | 2006138095 A1 | 12/2006 |
| WO | 2017129556 A1 | 8/2017 |
| WO | 2018193996 A1 | 10/2018 |

OTHER PUBLICATIONS

UKIPO, Search Report for GB 1903367.9, pp. 5 (mailed Sep. 4, 2019).

WIPO, PCT Form ISA210 International Search Report for PCT/EP2020/056550, pp. 6 (mailed May 4, 2020).

WIPO, PCT Form ISA237 Written Opinion for PCT/EP2020/056550, pp. 8 (mailed May 4, 2020).

WIPO, PCT Form ISA373 International Preliminary Report on Patentability for PCT/EP2020/056550, pp. 7 (mailed Aug. 25, 2021).

UKIPO, Search Report for GB 2112840.0 pp. 5 (mailed Sep. 21, 2022).

IPOS, Written Opinion for SG Patent Application Serial No. 11202108968R, pp. 13 (mailed May 30, 2023).

* cited by examiner

CONNECTION SYSTEM

This application is a 35 U.S.C. § 371 U.S. national stage patent application which claims the benefit of priority and is entitled to the filing date of International Patent Application PCT/EP2020/056550, filed Mar. 11, 2020, an application that claims the benefit of priority and is entitled to the filing date of GB Patent Application 1903367.9, filed Mar. 12, 2019, the content of each of which is hereby incorporated by reference in its entirety.

INTRODUCTION

The present invention relates to a connection system for flexible tubes, typically but not exclusively silicone tubes, and includes a method of connecting such tubes, and the fittings used in such a method.

BACKGROUND TO THE INVENTION

In the food, medical, pharmaceutical, cosmetics and personal care industries single use apparatus, or bio-disposable systems, are used in the batch preparation of some products. Similar systems are also used in the milk production system, in brewing and beverage production, and in the homecare industries, in the electronics industry, the food industry and the medical industry generally. Some systems are designed not for small batch production, but for permanent or semi-permanent installation, again in the foods, medical, pharmaceutical, cosmetics and personal care industries.

Single use apparatus includes flexible tubing, which is typically made from silicone, but may be made from other plastic materials, such as thermoplastics. Connection to other tubes or pieces of apparatus required in the production process are commonly made with flanged connectors which are clamped to each other, with a rubber gasket positioned between the flanges creating a seal. The flanged connectors include a hollow, usually barbed, spigot over which the flexible tube is placed in a fluid tight manner. This standard system is known as the tri-clover system. Initially the tri-clover system was developed for connection of multi-use components made from metal, typically stainless steel. However, more recently it was adapted for use with single use, bio-disposable systems using plastic materials or the like which can be sterilized by radiation, ethylene oxide or steam. However, other clamping devices are also used, including those that are secured by cable ties, quick connect systems, threaded systems, and other connecting systems.

Importantly, fluid passing through such a connection will come into contact not only with the tubes, but also the flange connectors and the gasket. These will typically be made from different materials, and in order to comply with regulations it will be necessary to carrying out testing for biocompatibility of the production line with each of the three different materials. If there is an alteration to the production process, for example a change in temperature or raw material, it could be necessary to repeat such testing on all of the three materials again.

In additional all such connection systems result in the creation of significant crevices at or around the joint, which can create stagnant areas, and potentially a loss of material.

More permanent systems may use similar apparatus, connected by flexible tubing clamped together. However, they also use semi-flexible or even rigid tubing that may be connected together using butt welding. This technique is difficult to use and very time consuming. Due to the nature of the liquids, solutions and fluids passing through the tubing, high grade materials must be used, and sterility achieved.

Flexible tubes are tubes which have flexibility but will spring back to the shape in which they were formed when a bending, flexing, or retaining force is removed. As such they undergo elastic deformation. Such tubes are said to have "memory". Thus, while such a tube can be bent round a corner, be folded in half, or be splayed open at one end, when the force urging this is removed, the tube usually returns to its original shape and dimensions. In addition, while the tube allows such bending, folding, and splaying it offer some resistance to this, which usually allows it to return to its original shape and dimensions when the force is removed.

A flexible tube is made from flexible material, and an important feature of flexible material, as mentioned above, is that is deforms elastically. This means that it is able to deform under a force; the deformation is not permanent, but resistance to the deformation is essentially permanent. This results in flexible materials being able to form a seal, as under application of a force, they will conform to any surface against which they are urged, maintain conformation which the force is maintained. This can create a seal. Two pieces of flexible material urged together form a very good seal.

There are various reasons for connecting two pieces of tube together. Typically, these include a change in the diameter of the tube to adjust the flow or provide the correct size for entry into another element of the system, such as a mixer or a filter.

It would be to desirable reduce the number of materials involved in such a joint, to reduce the bio-compatibility testing that is required for each production line. It would also be desirable to provide an easy-to-use sterile system that can be used in production lines and other industry procedures.

In addition, in the water industry and other industries where liquids, fluids and solutions are moved, there is a need for crevice-free connections using tubing.

The aim of the present invention is therefore to provide a connection system for flexible or semi-flexible tubing that minimizes the number of materials used in a connection. Specifically, the aim is to create a connection using only the tubes themselves to form the fluid tight connection and to achieve a near crevice free connection.

SUMMARY OF THE INVENTION

According to the invention there is provided apparatus for forming a sealing end from a length of flexible tubing, the apparatus comprising;
   a tubing support having
      a spigot sized to fit over the flexible tubing; and
     a sleeve sized to maintain an end of the flexible tube rolled back over the tubing support,
wherein the sleeve and tubing support are engageable with each other.

Typically, the spigot will be sized for a location fit over the flexible tubing and the sleeve will be sized for an interference fit over the end of the flexible tube rolled back over the tubing support. However, where the tube has a small internal diameter, the rolling back of the end can reduce the internal diameter. To avoid this, the tubing support may be provided as having an internal diameter slightly larger than the external diameter of the flexible tube, for example 5-20% larger, preferably 5-15% larger and most preferably 5-10% larger.

Usually, the tubing support will also include a lip extending substantially perpendicularly to the spigot. This can provide a stop for the rolled back end and may also provide a measure for the approximate distance for the length of the rolled back end. The lip can also provide a stop for the sleeve when pushed over the rolled back end.

Conveniently the connection between the tubing support and the sleeve may be between the lip and the sleeve.

Additionally, or alternatively, the sleeve may be provided with a lip extending substantially perpendicular to the sleeve. The sleeve lip may be sized to engage behind the rolled back end, again acting as a measure for the length of the roll back and the positioning of the sleeve relative to the tube support.

In some options, both the tubing support and the sleeve may be provided with a lip, both lips extending substantially perpendicular to the spigot and sleeve. The two lips may be arranged to engage with each other providing the connection between the elements. In such embodiments, the sleeve lip may be in the form of a rim and the support lip may be provided with a downwards step at its end distant from the roll back, the rim latching over the step.

Other forms of engagement between the tubing support and sleeve may also be used. For example, screw mechanism, clips, projections, and corresponding dimples can all be provided.

In use the tubing support can be placed over a length of tubing, with the tubing first entering the support from the end with the lip (if provided) and positioned such that the distal end of the spigot is spaced a short distance from the end of the length of tubing. The end of the tubing can then be rolled back on itself over the spigot of the tubing support. The sleeve can then be fitted over the rolled back end, securing the same. Once in place formations on the sleeve and tubing support mate to connect the elements together. The rolled back end provides a sealing end or surface, namely the face created by the rolled back end, which can be urged against another such sealing end, or indeed other surface, to form a fluid tight seal.

The connection between the sleeve and the tubing support is designed to prevent any accidental removal of either element and/or to ensure that the elements are in the correct place at the end of fitting. Typically, the connection will be between the sleeve and the support lip, although the connection could be between the sleeve and the spigot, particularly if no lip is provided. The sleeve may include a projection adjacent one end, the end that will connect to the lip in use, and the lip will have a corresponding channel or dimple. The projection may be continuous or may be discontinuous. Alternatively, the sleeve may be provided with a rim at one end, the end that will contact the lip in use, and the lip may be provided with an edge or a step, such that on introduction of the sleeve, the rim latches over the edge or step, holding the sleeve in place and confirming correct fitting. In other alternatives, mating screw threads may be provided on the sleeve and the lip.

The invention thus also provides apparatus for forming a sealing end from a length of flexible tubing, the apparatus comprising;
 a tubing support having
  a spigot sized to fit over the flexible tubing; and
  a lip extending substantially perpendicularly to the spigot; and
 a sleeve sized to maintain an end of the flexible tube rolled back over the tubing support.

For connecting two tubes, having rolled back ends, a clamping system can be used. While other clamping systems can be used, the present invention can be used with the tri-clover system. As such the apparatus, according to a second aspect, can further comprise
 a flanged connector having
  a catch sized to engage with the tubing support and/or sleeve;
  a tubular section, designed in use to be parallel to the length of tubing; and
  a flange, sized for clamping to another flange of another flanged connector.

For use, the flanged connector can be drawn up behind the tubing support with the catch of the connector abutting the lip of the tubing support. The rolled back ends of the tubes provide a sealing joint between the tubes, which are held in place by clamping the flanges of the flanged connectors together with a standard bio-disposable clamp, namely a tri-clover clamp. Previously such a connection would necessarily include a gasket placed between the flanges; the seal being created by the gasket. In accordance with the invention, as the sealing is achieved by the abutting ends of the rolled back tubes, the gasket is no longer required. Nevertheless, the gasket may be included out of habit. Production flow entering the joint will be in contact with the flexible tube, and with the rolled back ends of the two tubes forming a fluid tight abutment joint, the fluid will not contact any other materials in the joint.

In a further alternative, the sleeve can be in the form of a flanged connector. The flanged connector will be sized to maintain an end of the flexible tube rolled back over the tubing support, typically an interference fit. The distal end of the sleeve/flanged connector will be provided with means for engagement with the tubing support, typically a lip of the tubing support. An upper surface of the sleeve/flanged connector, namely outwards from the tube, will be shaped in the form of a flanged connector and connectable to other flanged connectors, either with or with a gasket in between.

This arrangement enables two rolled back ends to be connected together, with the rolled back ends abutting to form a seal. Pairs of sleeve flanged connectors may be held together with standard tri-clover clamps, with or without a gasket in between. Alternatively, the use of a flanged connector enables a tube having rolled back end to be connected to a non-rolled back tube, connected to a standard flanged connector using the tri-clover system. (While this will rarely be done, it is possible.)

In a further alternative, a sleeve/flanged connector as described above, can be used to connect rolled back end to another flanged end, for example on a filter or other element in a system. To enable such use, the sleeve/flanged connector is set back slightly from the rolled end to enable the rolled end to seal against the additional element, for example the flange of a filter. The flange is provided with a projection for spacing from the flange of the other element, allowing the flanges to be connected with a tri-clover clamp, with or without a gasket, the seal be provided by the rolled end against the other element. In a yet further alternative, connection to a flat surface of another element can also be made with the sleeve/flanged connector, as above with the rolled end protruding slightly from the sleeve/flanged end which is set back. This enables the rolled end to seal against a flat surface. Advantageously, a projecting ring, which may be continuous or discontinuous, may be provided on the flange surface, to mate with a corresponding dimple in the flat surface, for location. The flanged connector can then be clamped to the flat surface using a clamping system.

This flat surface may be a flanged connector, for example such as used in the currently standard tri-clover system.

Consequently, the flanged surfaces can be held together with a standard clamp of the tri-clover system. This thus allows connection between a rolled end and the currently standard tri-clover system.

A further alternative for connection to the tri-clover system, or indeed any system using a flanged connector is also provided. A blank end is provided, having a flat surface against which a rolled end can seal, the blank end having a through passage for flow of fluid. The blank end will be sized to enable clamping to a rolled end supported by a tube support and sleeve as described above. This enables the rolled end and the blank end to be held together using a clamp specifically designed for holding a pair of rolled ends together in sealing arrangement. Such a clamp is described in our currently unfiled application. The blank end is provided with an extension to a flanged connector. This enables the flanged connector of the blank end to be connected to another flanged connector, for example of a tri-clover system, or any other flanged connector.

Alternatively, other clamping systems can be used. For example, clamps specifically designed to hold together a pair of rolled back ends as above described.

Preferably tubing supports with different sized spigots may be provided to allow for different sizes in tube diameter. Preferably the spigots may be provided with distal ends adapted to abut tubing having a smaller or larger diameter. For example, a spigot may incorporate an end thickened on the outside for abutment with another spigot sized for a larger diameter of tubing. Alternately a spigot may incorporate an end thickened on the inside for abutment with another spigot sized for a smaller diameter of tubing. The thickening may be in the form of a taper, which increases or decreases the thickness of the spigot. The taper may increase the distal end of the spigot towards the centre of the spigot, or away from the centre of the spigot. Alternatively, the spigot may be thickened along its entire length.

It has been found that it is generally more convenient and typically creates smoother flow paths to increase the diameter of smaller tubes by using an expanding spigot, than to reduce the diameter of larger tubes, when joining tubes of different diameters, although both or any option can be used. It is also advantageous for smooth flow paths to provide rounded edges to the spigot when thickened spigots are used.

Preferably sleeves of different sizes, i.e., thicknesses, may also be provided. The size of the sleeve will be dependent on the diameter of the tubing and the thickness of the tubing.

Depending on the type of connector used, it is advantageous to have the outer diameter of the sleeve the same on two tubes to be connected, even if the tubes have different diameters. As such sleeves of different thicknesses can be used to enable the outer diameter of two connections to be the same. The inside diameter of the sleeve will be sized to secure the rolled back end against the tubing support.

In some embodiments the spigot on the tubing support may incorporate a series of protrusions or barbs to hold the rolled back end on the spigot. However, in other embodiments these will not be included and are not believed to be necessary.

In some embodiments the sleeve may incorporate a small protrusion or pimple on its inside end to engage in a dimple in the spigot. This acts as an aid to prevent removal of the tubing support and sleeve combination. While advantageous is connecting the tubing support and sleeve together, and in creating a latching effect to indicate when the two elements are ideally positioned, this is not essential.

Typically, the length of rolled back end is in the range of 4-16 mm, preferably 6-12 mm, and more preferably 6-10 mm.

As the tubing is flexible tubing, it will be resistant to being rolled back, and if rolled back a short distance only, on removal or any rolling or retaining force, will unroll. However, if the tube is rolled back a longer distance, the resistance of the tube to deformation will prevent unrolling, as this would at least initially involve a greater deformation. However, such a rolled back end is not very stable, as only a small amount of force would be required to push the roll back towards the end, and the length at which it would unroll in the absence of additional force.

While the tube can be rolled back a short distance only, typically it is desirable to roll a tube back by a distance such that it is stable, i.e., will not unroll. This distance will vary depending on the diameter of the tube and the material from which the tube is made. However, this distance is usually substantially in the range of 75-100% of the external diameter of the tube. As such the preferred length of the roll back is 50-125% of the external diameter of the tube, more preferably 60-115% of the diameter and most preferably 70-105% of the diameter of the tube. In preferred examples the length of the roll back is 70-90% of the external diameter of the tube.

As the tube support and sleeve are design to support, maintain and protect the rolled back end, they need to be sized to accommodate the rolled back end. As such the length of the tube support from a distal end to any formation enabling connection to the sleeve, in particular the lip, is sized to support the roll back. The length of the tube support is very slightly longer than the desired length of the roll back. Thus, the length of the tube support is substantially 73-102% of the external diameter of the tube. As such the preferred length of the roll back is 48-127% of the external diameter of the tube, more preferably 58-117% of the diameter and most preferably 70-105% of the diameter of the tube. In preferred examples the length of the tube support is 68-92% of the external diameter of the tube.

As the tubing support, sleeve and the flanged connector will not come into contact with the flow path, they may be made of any supportive material, typically one that can be sterilized. Bio-disposable systems are typically sterilized using radiation and thus suitable materials include materials that can be irradiated, including plastic materials. Typically, the plastic may be polypropylene or polyvinylidene difluoride (PVDF). Where the sterilization will be via heat treatment, the tubing support and flanged connector may be made of metal, for example stainless steel and/or plastic.

The flexible tubing may be made of any flexible material. The properties of flexible tubing and flexible material are set out above and are well understood in the industry.

Such tubes are typically made of silicone or thermoplastic. However, the flexible tube may also be made of a plastic material incorporating a plasticizer for increased flexibility, or reinforcement, such as braided, tubing. In further alternatives, the tubing may be made from latex or PVC.

In addition, the diameter of the tubing may be any size generally used in such systems. Such tubing is generally defined by its internal diameter. As such tubing having an internal diameter of ⅛" (3.175 mm), ¼" (6.35 mm), ⅜" (9.525 mm), ½" (12.7 mm), ¾" (19.05 mm), 1" (25.4 mm) or 2" (50.8 mm) may be used. Preferably the tubing has an internal diameter of ⅛" (3.175 mm), ¼" (6.35 mm), ⅜" (9.525 mm), ½" (12.7 mm), ¾" (19.05 mm), 1" (25.4 mm) or more preferably ⅛" (3.175 mm)-¾" (19.05 mm) diameter. Larger tubing could also be used, for example having an internal diameter of 2-3 inches (50.8 mm-76.2 mm). Currently standard tubing diameters is given as a measurement in inches. However, tubing having a diameter given in mm could also be used. Such tubing will typically have a size range of 2 mm-20 mm. All tubes must be flexible, as discussed above.

Rolling back the end of tubing may not affect the internal diameter of the tube, even the end of the tube. This is the case for tubing having larger internal diameters. The size of such tubing depends on the material from which the tube is made and its flexibility. With tubing made from silicone, the internal diameter at which the internal diameter is not affected by rolling back is approximately 5/8" (15.875 mm). Thus, for such tubing having an internal diameter of 1/2" (12.7 mm) or below, the rolling back of the end may create a slight reduction in the internal diameter of the tube. This reduction in internal diameter is very slight and should not significantly interrupt flow in the tube.

For tubes where the rolling back of the end does not affect the internal diameter, the tubing support will generally be sized for a location fit over the flexible tube, and the sleeve will be sized for an interference fit over the rolled back end.

However, for tubes of smaller diameters where rolling back of the end does result in a small reduction in the internal diameter, in order to improve flow and reduce turbulence, it is advantageous to avoid any unintended reductions in internal diameter of the tube. Thus, for tubes of smaller size, where a reduction in internal diameter is experienced, a tubing support and a sleeve having an internal diameter slightly greater than a location fit over the flexible tube and an interference fit over an end of the flexible tube rolled back over the tubing support can be used. This increase in size will be dependent on the size of the tube and the material from which it is made.

For example, for a 1/2" (12.7 mm) tube, namely a tube having an internal diameter of 1/2", with have an external diameter of 0.717" (18.2 mm), for an interference fit, the expected internal diameter of the tubing support would be 0.717" (18.2 mm). However, to avoid any reduction in the internal diameter of the tube, a tubing support having an internal diameter of 0.756" (19.2 mm) should be used. Similarly, for a 1/2" (12.7 mm) tube, rolled back over the tubing support, the spigot of which having a thickness of 0.024" (0.6 mm), the internal diameter of the sleeve would be expected to be 1" (25.4 mm). However, in order to avoid reduction of the internal diameter of the tube and using the tubing support described above, a sleeve with an internal diameter of 1.04" (26.4 mm) can be used. As will be clear, the internal diameter of both the tubing support and the sleeve have been increased by 1 mm.

Similarly, for a 1/4" (6.35 mm) tube, namely a tube having an internal diameter of 1/4", with have an external diameter of 0.488" (12.4 mm). For an interference fit, the expected internal diameter of the tubing support would be 0.488" (12.4 mm). However, to avoid any reduction in the internal diameter of the tube, a tubing support having an internal diameter of 0.508" (12.9 mm) can be used. Similarly, for a 1/4" (6.35 mm) tube, rolled back over the tubing support, the spigot of which having a thickness of 0.024" (0.6 mm), the internal diameter of the sleeve would be expected to be 0.74" (18.8 mm). However, in order to avoid reduction of the internal diameter of the tube and using the tubing support described above, a sleeve with an internal diameter of 0.76" (19.3 mm) can be used. As will be clear, the internal diameter of both the tubing support and the sleeve have been increased by 0.5 mm.

For completeness, for a 1" (25.4 mm) tube (namely a tube having a 1" internal diameter), this will have an external diameter of 1.26" (32 mm). As such, a suitable tubing support will have an internal diameter of 1.26" (32 mm). Where the thickness of the spigot is 0.0236" (0.6 mm), the sleeve may have an internal diameter of 1.57" (39.8 mm). Using this arrangement, namely with no increase in the size of the internal diameter of the tubing support comparted to the outside diameter of the tube, no decrease in the internal diameter of the tube is found when its end is rolled back.

For other sizes of tubing, appropriate increases in the internal diameter of the tubing support and sleeve can be used where necessary, as will be easily determined by the skilled person.

Alternatively, a slight flare may be applied to the end of the spigot of the tubing support and the sleeve.

According to a third aspect of the invention there is provided a method of connecting two lengths of flexible tube, the method comprising
 rolling the end of each length of the tubing back on itself; and
 using the rolled back ends to create a fluid tight connection.

Preferably the rolled back ends are supported using the tubing supports and sleeves defined in the first aspect.

Preferably the connection is formed by urging the rolled back ends together by clamping the flanged connectors of the first aspect, engaged with the tubing supports and/or sleeves of the first and second aspects.

According to a further aspect of the invention there is provided a method of forming a sealing end from a length of flexible tubing, the method comprising
 pushing a tubing support according to the first aspect over an end of a tube such that the lip (where provided) is furthest from the end of the tube and the spigot is positioned a short distance from the end of the tube;
 rolling the end of the tube back over the spigot, the length of rolled back tube not extending past the lip (where provided) or end of the spigot;
 pushing a sleeve according to the first aspect over the rolled back end; and
 connecting the tubing support and sleeve using the means provided.

To form a fluid tight seal from two rolled back ends, such ends can be clamped together using the apparatus according to the second aspect. Alternatively, over clamping means can be used, for example clamps designed for securing two rolled back ends in sealing alignment.

It has been found that where the tubing is made from PVC, or other similar material, the rolled back end is less stable. In such cases a length of silicone tube can be used to cushion the PVC on the tubing support. The seal can be formed between the two-abutting rolled back ends of the PVC tubing. The PVC tubing can be rolled back over a spigot according to the invention, over which a short length of silicone tubing is placed, secured by a sleeve. This provides a stable rolled back end when the tubing is PVC. While this system can be advantageous, it is not essential.

In addition, tubes made from PVC may not be sufficiently flexible and elastic to form a seal, depending upon the composition and formulation of the PVC. In such cases, and internal lining of a silicone tube can be used, with this lining then rolled back over a tubing support placed over the PVC tube. This can be secured with a sleeve as described above. This also applies to other tubes of limited flexibility and elasticity, namely tubes that are semi-flexibly or rigid. Grooves may be provided in the semi-flexible or rigid tube, with projections provided in the inside of the spigot of the tubing support for locating and securing the tubing support on the semi-flexible or rigid tube. Other arrangements for connecting the tube support and the semi-flexible or rigid tube may also be used, although such connection is not essential.

The rolled back-end seal can also be used as a connection and lining in semi-flexible or even rigid tubing. A length of silicone, or other flexible tubing can be passed through the semi-flexible or rigid tubing and used to form a connection to another length of semi-flexible or rigid tubing also containing a lining of silicone. In such cases the length of the spigot of the tubing support may be reduced. Additionally, or alternatively, the spigot may be provided with projection to mate into indentations in the semi-flexible or rigid tubing for securement. The flexible tube lining can be rolled back over the end of the semi-flexible or rigid tube and secured by the tubing support and sleeve.

As discussed above, rolled back ends can be used to connect two tubes together, for example to extend the length of a tube or to change the diameter of the tube through which liquid will flow. Rolled back ends may also be used to create a seal against other surfaces against which they are urged. As a result, a full production system, or part thereof can be created using all or mostly seals utilising rolled back ends.

In such a system valves will be required, and a valve can be created using a length of tubing having two rolled back ends, and a clamp therebetween. Thus, according to a further aspect of the invention there is provided a valve comprising:—
  a length of tubing, each end of the tubing being rolled back and supported by the apparatus of the first aspect;
  a clamp positioned between the ends of the tube and sized to press the tube to cause is collapse, blocking the tube, or allow the tube to remain in its open state allowing flow through the tube or any partial restriction thereof. Alternatively, could have roll back to additional separate valve.

The clamp may be any suitable clamp capable of crushing to prevent flow therethrough. Typical clamps have plungers which extend down from a top of the clamp to a seat of the clamp on which the tube may be placed.

In addition, in such a system an end cap is also required, which can be created from a length of tubing having one rolled back end, and a clamp fixed in a closed position spaced a short distance from the rolled back end. Thus, according to a further aspect of the invention there is provided an end cap comprising:—
  a length of tubing, one end of which is rolled back, the roll back being supported by the apparatus of the first aspect; and
  a clamp compressing the tube such that is it collapsed on itself and sealed.

DETAILED DESCRIPTION OF THE INVENTION

To help understanding of the invention, specific embodiments thereof will now be described by way of example and with reference to the accompanying drawings, in which.

EXAMPLES

Figure 1:
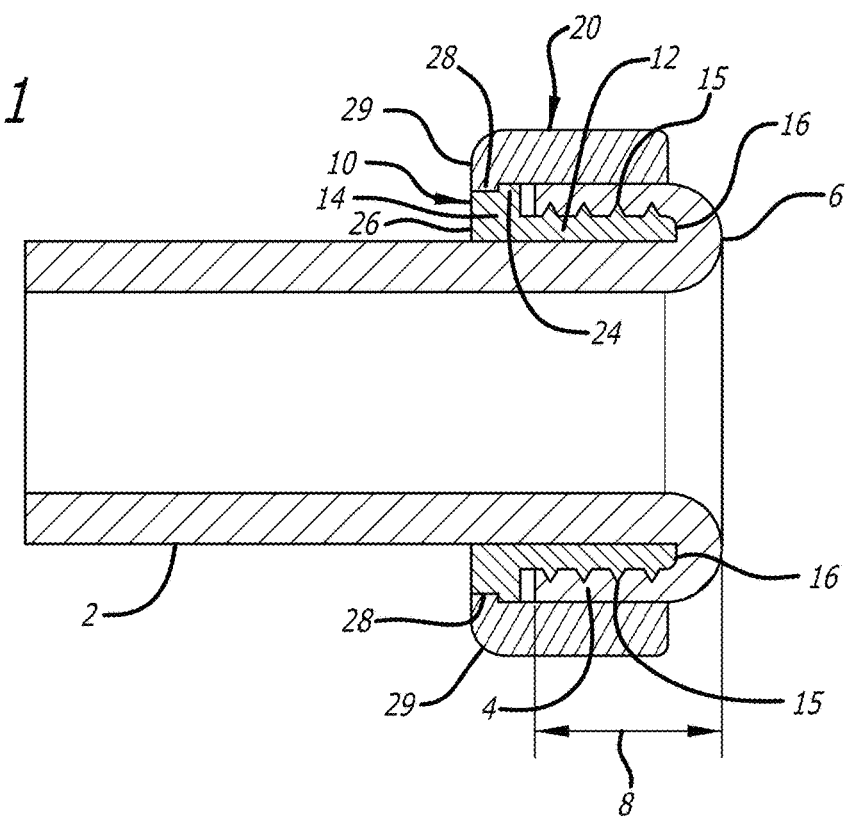
FIG. 1 is a cross-sectional view one end of a flexible tube rolled back over a tube support and held by a sleeve according to the invention providing an abutment surface.
Figure 2:
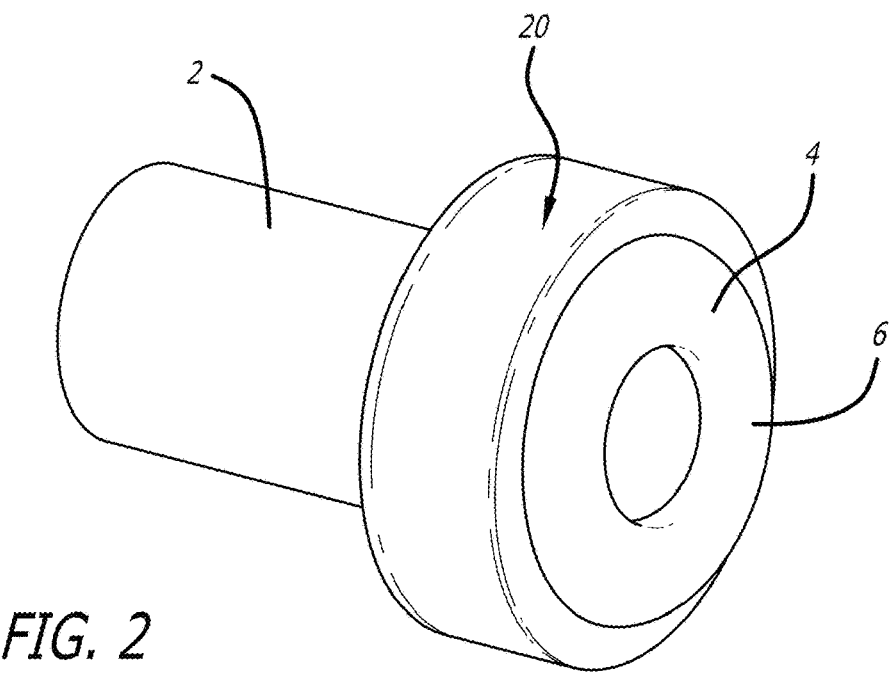
FIG. 2 is a perspective view of the end of the flexible tube of FIG. 1.
Figure 3:
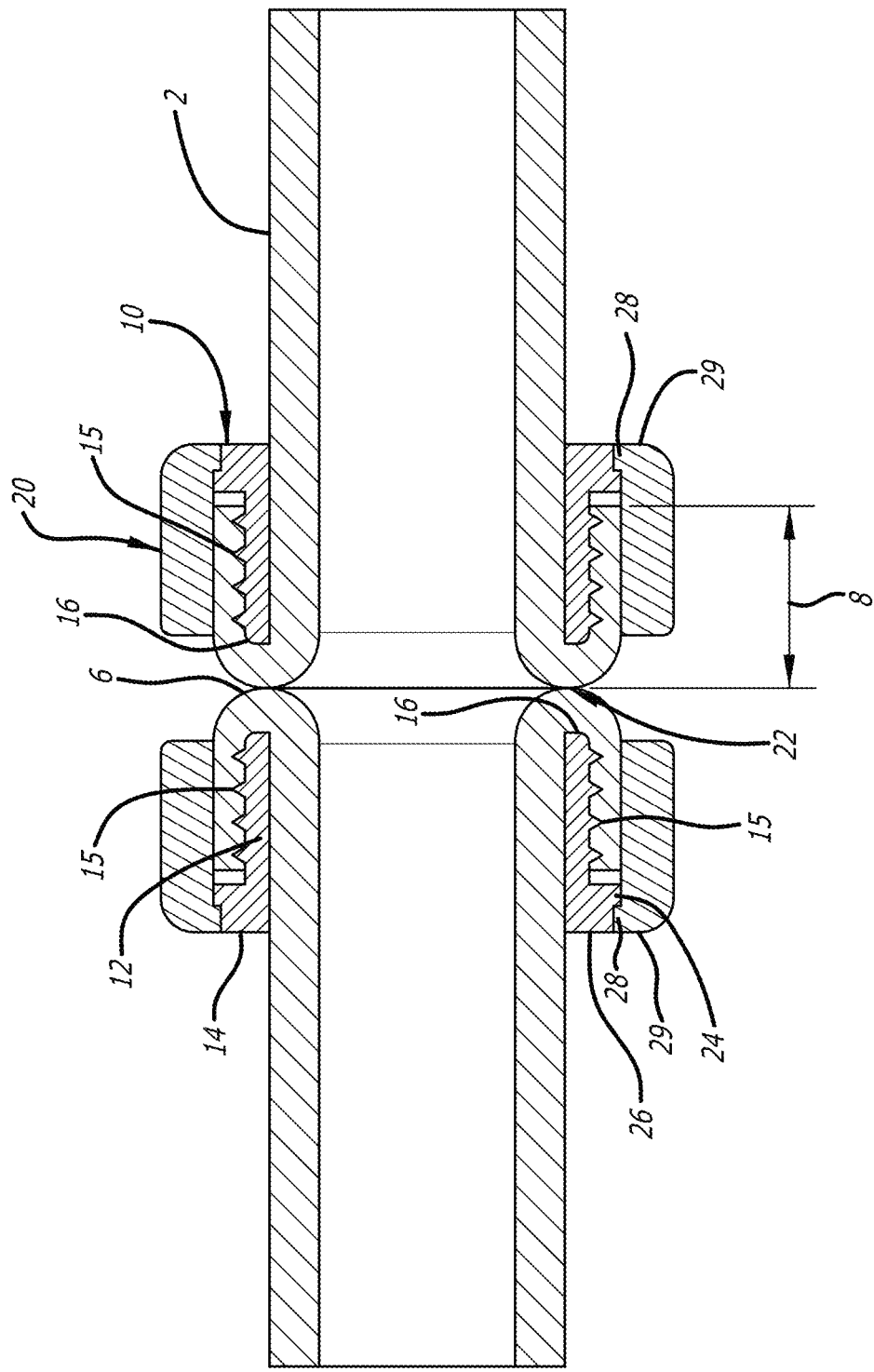
FIG. 3 is a cross-sectional view of a connection between two flexible tubes according to the invention.

Referring to FIGS. 1-3, the seal shown in FIG. 3 is based on abutment between the rolled back ends 4 of two lengths of flexible tubing 2, as shown in FIGS. 1 and 2. By rolling back the end of a length of flexible tube 2 an abutment surface, namely a sealing end or sealing surface 6 is created. This surface is sufficiently large, and the flexible tube material is sufficiently elastic, supple, and conforming such that the abutment surface 6 is able to create an air and fluid tight seal when urged against another sealing surface, such as another abutment surface 6 formed from the rolled back end of another tube.

In order to support the rolled back end, and to provide a means of urging the abutment surface 6 created by the rolled back end into a sealing arrangement, a tubing support 10 is provided. This is sized to be a tight or transition fit over a length of tubing 2, and tubing supports 10 may be provided in a range of different sizes appropriate to the flexible tubing to be used.

The tubing support 10 comprises a spigot 12 having a lip 14, substantially perpendicular to the spigot, extending away from the tubing. In use, the tubing support 10 is pushed over the end of the tube such that a distal end 16 of the spigot 12 is positioned slightly back from a distal end of the tubing by a distance equating to the intended roll back. The tubing is urged into the support at the lip end first, so this is away from the end of the tube. The tubing can then be rolled back over the end of the spigot 12. This may be done by hand, or a tool or apparatus (not shown) may be used to roll back the end.

In some embodiment, projections, or small barbs 15 on the outer surface of the spigot may assist in holding the rolled back end of the tube in position.

The rolling back of the end of the tube 2 creates and abutment surface 6, which when held against another abutment surface forms a fluid tight seal.

Once the tube support 10 has been positioned on the tube 2 and the end of the tube 4 rolled back, this creates an abutment 6 surface formed from a flexible material that will form a seal 22 to a corresponding abutment surface, or indeed to another sealing surface.

The rolling back of a tube on itself will create a stable structure once the end has been rolled back to a sufficient length 8. This roll back length 8 will be dependent on the material of the tube, its thickness and diameter. Standard tubes generally have a wall size of ⅛" (3.175 mm). This size currently represents 70-80% of the market in such flexible tubes. Other tubes may have a wall size of 1/16" (1.5875 mm) or 3/16" (4.7625 mm).

With tubes standard in the food, pharmaceutical, cosmetics and brewing industries, for example which are typically made from silicone and have a ½" (12.7 mm) internal diameter. As discussed above, the length of the roll back is approximately equal to 75-100% of the outside diameter of the tube. Thus, for a tube having an external diameter of 1" (25.4 mm) a typical roll back would be ¾"-1" (19.05-25.4 mm). Typically, a roll back of substantially 75% of the external diameter of the tube is used. This length is dependent in part on the thickness of the tubing wall and the suppleness of the tubing. More flexible tubing is easier to assemble and thus is preferred within the industries.

As discussed above, flexible tubing will be resistant to being rolled back, and if rolled back a short distance only, on removal or any rolling or retaining force, will unroll. However, if the tube is rolled back a longer distance, the resistance of the tube to deform will prevent unrolling, as this would involve a greater deformation. However, such a rolled back end is not very stable, as only a small amount of force would be required to push the roll back towards the end, and the length at which it would unroll in the absence of additional force. While the tube can be rolled back a short distance only, typically it is desirable to roll a tube back by a distance such that it is stable, i.e., will not unroll. This distance will vary depending on the diameter of the tube and the material from which the tube is made. However, this distance is usually substantially in the range of the external diameter of the tube However, for higher pressure systems sturdier tubing is required, which is less flexible and less easy to assemble generally. For high pressure systems internally, braided tubing may be used. Tubing of higher stiffness also has stronger conformity memory and thus is more likely to become detached from connectors and the like. The presence of the braiding in the tubing tends to shrink or draw back at the cut ends. This action is also likely to encourage the tubing to unroll. However, the urging a rolled end against an abutment surface, for example another rolled end, significantly reduces the ability of the rolled end to unroll. This is particularly the case for internally braided tubes, where the contraction of the braiding adjacent the end can encourage unrolling.

For some tubes of tubing that are still flexible as discussed above, but stiffer than standard flexible tubes while retaining elasticity, the application of a small amount of heat may be beneficial when rolling back the end of the tube.

In order to provide additional stability, the apparatus also includes a sleeve 20, positioned over the rolled-back end of the tube. This reduces the capacity of the tube to unroll. The rolled back end of the tube 2 is held between the sleeve 20 and the spigot 12 of the support 10.

Tubes may be rolled back using a former (not shown) which can roll back a tube 2 a sufficient distance over a tubing support 10. The same or a different former can also be used to insert a sleeve 20.

To reduce the possibility of removal of the support 10 and sleeve 20 combination, the two elements may be connected together. As shown, the lip 14 of the tubing support 10 is provided with a downwards step 24 adjacent is back edge 26. The sleeve 20 is provided with a projecting rim 28 adjacent is end 29. When the tubing support 10 is positioned over the tube 2, the end of the tube is rolled back over the tubing support 10 and the sleeve 20 is positioned over the rolled back end 4, the rim 28 of the sleeve clips over the step 24 of the lip 14 securing the sleeve 20 in position.

Alternative methods of securing the tubing support 10 and the sleeve 20 may be used. For example, although not shown, a channel can be provided in the lip 14 and an extended ring can be provided in the sleeve, which fit together once the sleeve has been correctly fitted. Alternatively, and also not shown, the channel may be provided on the sleeve 20 and the extended ring, either continuous or non-continuous, may be provided on the support 10.

This connection may provide an element of certainty that the device has been correctly fitted as the user is able to feel or hear the elements, namely the lip and ring, fitting into each other. However, due to the forces on the rolled back end, and the presence of the tubing support and sleeve, this connection between the tubing support and sleeve is not necessary.

Figure 4:
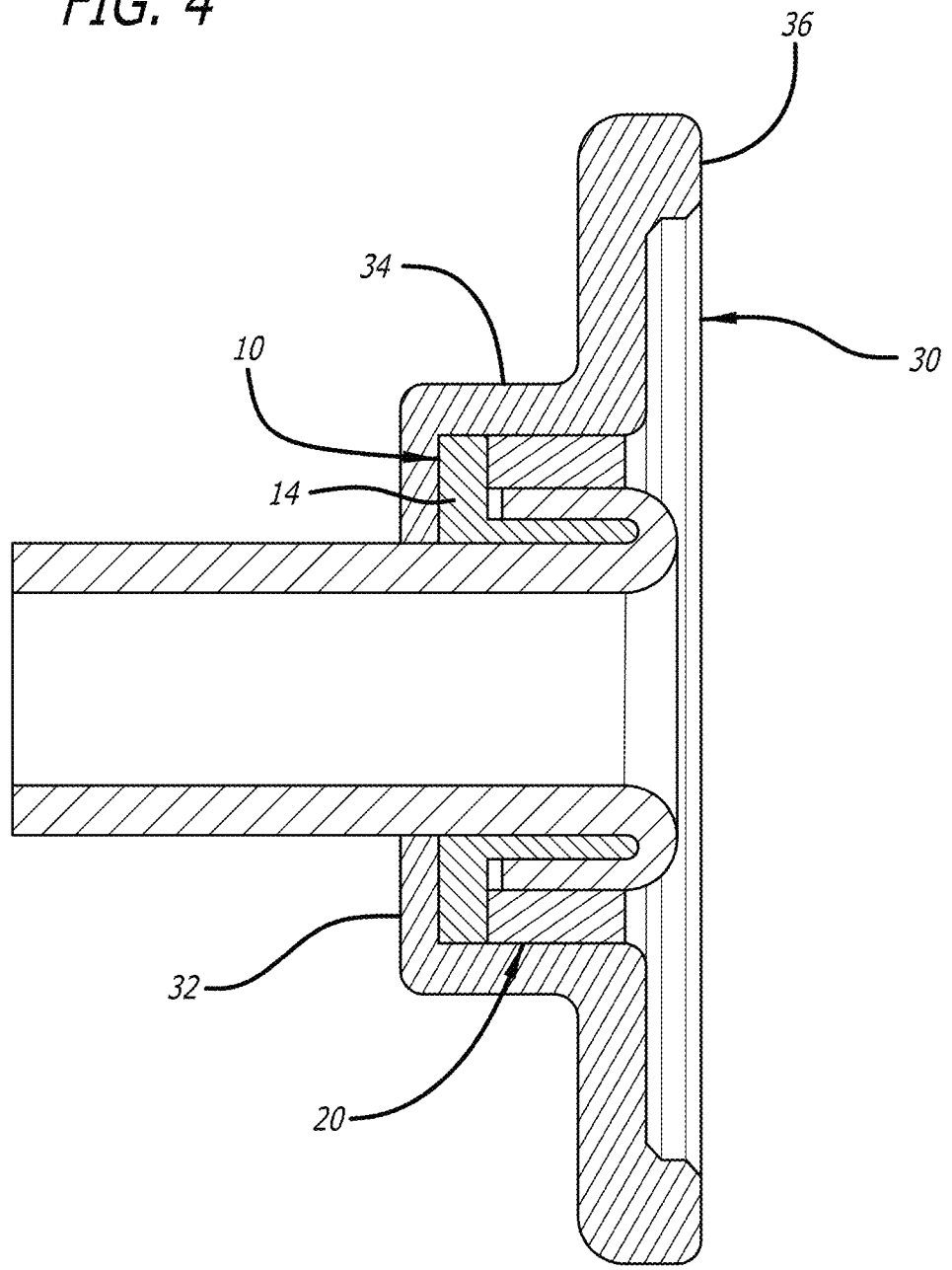
FIG. 4 is a cross-sectional view of the tube of FIG. 1 further including a flanged connector.

As shown in FIG. 4, a flanged connector 30 may be provided for connection to another flanged connector. A flanged connector 30 comprises a catch 32, designed to fit behind (in relation to the connection) the lip 14 of the tubing support 10, a tubular section 34 which connects the catch 32 to a flange 36 extending outwards from the connection.

Pairs of flanges 36 can be held together using the standard industry clamps (not shown). Whilst in prior art arrangements flanged connectors were provided with a gasket to create a seal, in the invention the seal is created between the rolled back ends. As such no gasket is necessary if two rolled back ends, such as shown in FIG. 3, are being used to form the connection. However, a gasket may still be used. Such clamps are generally known in the industry as tri-clover clamps, even when made of a plastic material such as described in EP1230505. The use of the flanged connector also enables connection of a tube having a rolled back end to another element of a production system not having a rolled back end. In such a case a gasket would not be necessary, as this would create the seal.

The clamp holds the flanges 36 together and in turn the flanges 36, acting through the tubular sections 34, urge the catches 32 against the lips 14 of the tube supports 10, urging the tubing supports 10 together, and thus the abutment surfaces 6 of the rolled ends of the tubes 2 together, forming the fluid tight seal 22.

Other forms of clamping mechanism can be used, with or without the flanged connectors. For example, the flanged connectors can be held together using male to female connectors, clamps held together by cable ties, quick connect fittings, screw threads and any other form of clamping or securing system. Alternatively, other clamping arrangements specifically designed for use with the tubing support 10 and sleeve 20 can be used.

In the embodiment shown in FIG. 4, no connection is provided between the support 10 and sleeve 20. In all other aspects these elements, 10, 20, are identical to those shown in FIGS. 1-3. Such a connection could, and usually will, be provided. As such a channel or series of projections or ring could be provided in the support 10 and a ring, series of projections or channel could be provided in the sleeve 20.

Figure 5:
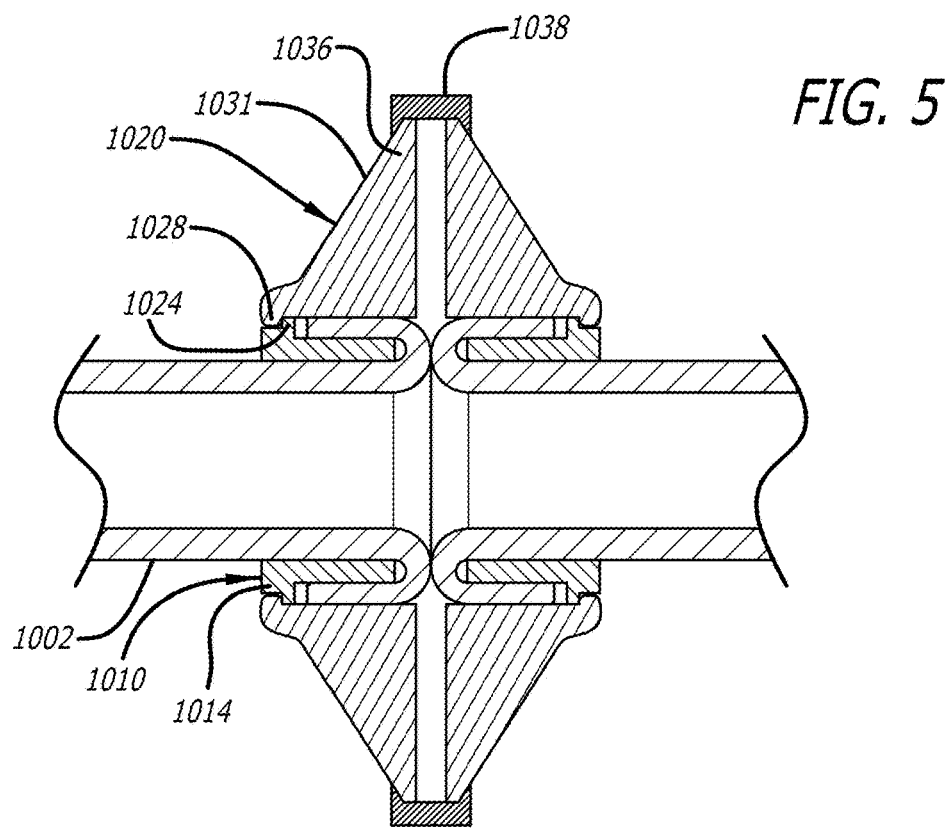
FIG. 5 is a cross-sectional view of an alternative arrangement incorporating a flanged connector.

In a further alternative, shown in FIG. 5, the tubular section of the flanged connector 30, and in particular the tubular section 34, can act as the sleeve.

As shown in FIG. 5, the tube 1002 is rolled back over a tubing support 1010, the tubing support being provided with a lip 1014, and the lip 1014 having a step 1024. A sleeve 1020 is provided, having a rim 1028, which clips over the step 1024 in use, as described above. Most sleeves have a flat upper surface, for example as shown in FIG. 1-4. However, as shown in FIG. 5, the sleeve 1020 is in the form of a flanged connector, and thus its upper surface 1031 is in the form of a flanged connector 1036. This then allows connection to another flanged connector. The depth of the flange will be set such that two rolled back ends supported on tubing supports with sleeves in the form of flanged connectors, will abut to form a seal, on clamping of the flanged connectors together. The flange will generally be of a size and shape such that an industry standard tri-clover clamp 1038 can be used to clamp a pair of such rolled back ends supported by tubing supports and sleeves having flanged connectors. Alternatively, any other of clamping arrangement can be envisaged. When using flanged connectors, it is standard to incorporate a gasket between the flanged connectors. When two rolled back ends are connected using flanged connectors as hereabove described, a gasket is not required, although may be present.

This arrangement also allows for a rolled back end having a flanged connector, either as described with reference to FIG. 4 or FIG. 5 to be connected to a tube fitted to another standard flanged connector, typically over a barbed end. In such an arrangement a gasket will be required.

The provision of a flanged connector to a rolled back end enables connections will rolled back ends to be integrated into the industry standard tri-clover system, and the variations thereon.

Figure 6:
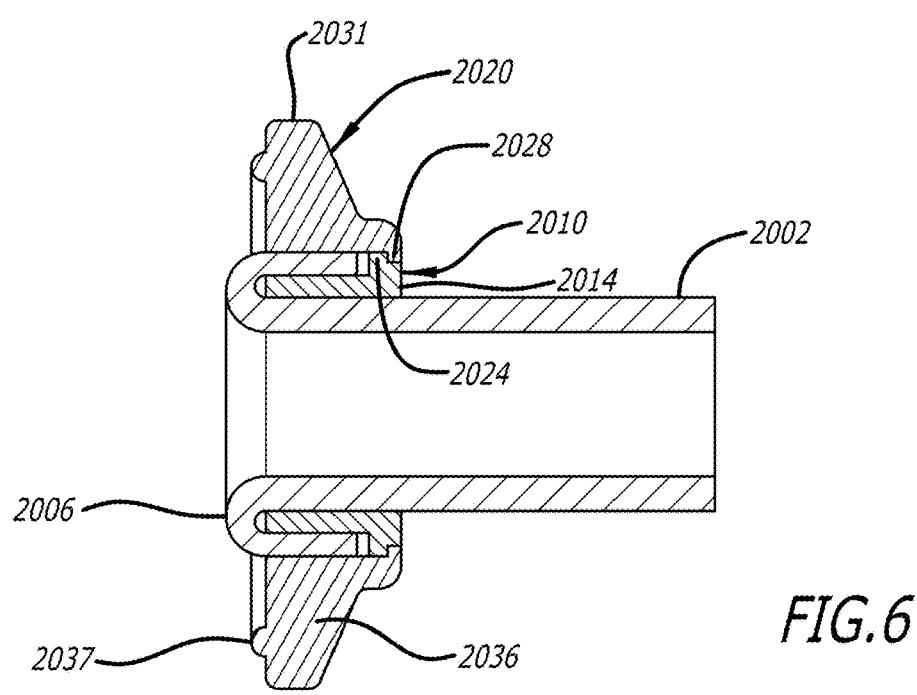
FIG. 6 is a cross-sectional view of a further alternative connector having a flanged connector.

FIG. 6 shows a further arranged using a flanged connector, the flanged connector being adapted to connect to an industry standard piece of equipment such as a filter, such as made by Pall. Connection can also be made to other filters, clamps, valves, elbows, laterals, manifolds, sieves, meshes, and indeed any other device having a flanged connector. As shown the tube 2002 is rolled back over a tubing support 2010, the tubing support being provided with a lip 2014, and the lip 2014 having a step 2024. A sleeve 2020 is provided, having a rim 2028, which clips over the step 2024 in use, as described above, holding the tubing support 2010 and the sleeve 2020 together. The sleeve 2020 is in the form of a flanged connector, and thus its upper surface 2031 is in the form of a flanged connector 2036. As shown the flange 2036 is provided with a projecting ring 2037, which may be continuous or discontinuous, which can mate into a corresponding depression in a standard piece of equipment, locating the flange and thus the tube thereagainst. The flange 2036 is set back slightly from the rolled back end, with the projecting ring 2037 being just back from the rolled end. This enables the rolled end 2006 to be urged against a flat surface of the standard equipment, forming a seal, and to be held in position.

Some standard pieces of equipment, such as filters, are provided with flanged connectors. Typically, the flanged connector includes a flat surface surrounding an opening to the equipment. Usually, a circular groove is provided surrounding the flat surface for locating and holding a gasket. Traditionally a connection is made to such a flanged connector by securing another flanged connector to the end of a tube, typically over a barb, placing a gasket between the two flanges and clamping them together, using a standard tri-clover clamp. The flange as shown in FIG. 6 enables a rolled end to be sealed against the flat surface surrounding the opening of a standard flange. The projecting ring 2037 locates into the circular groove ensuring correct location of the rolled back end. The two flanges can then be connected using a standard tri-clover clamp.

Figure 7:
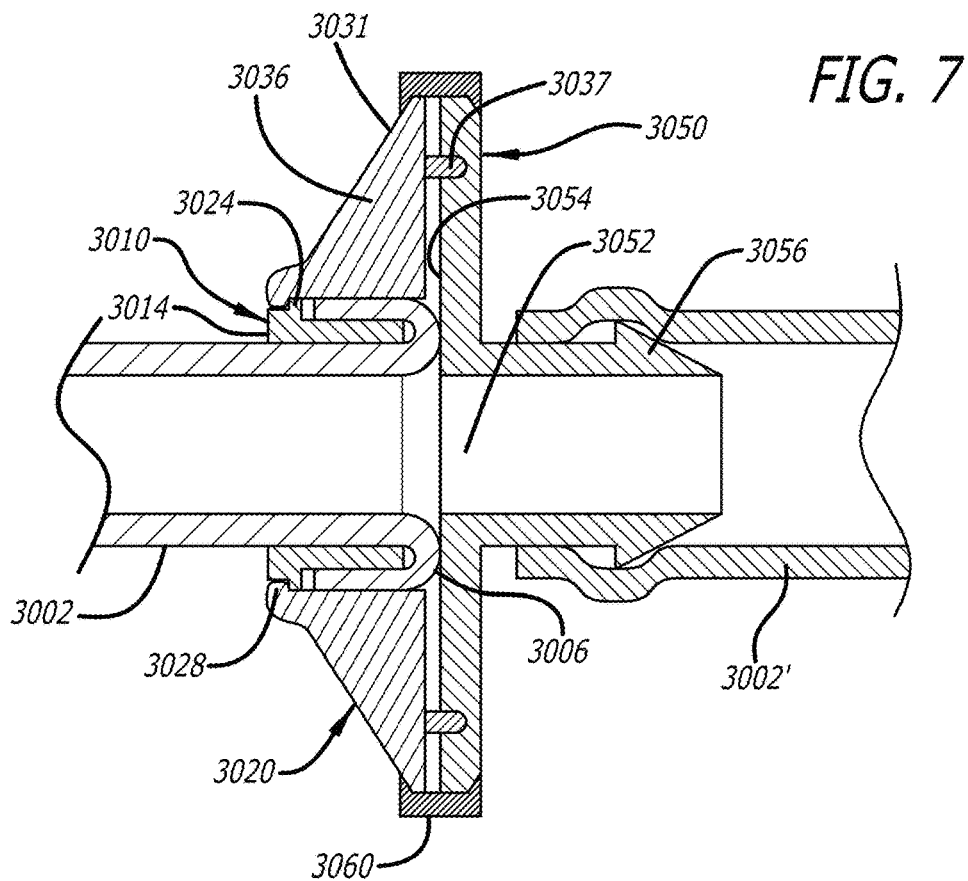
FIG. 7 is a cross-sectional view of a tube support connected to a flanged connectors.

FIG. 7 shows an arrangement very similar to that of FIG. 6, in which a rolled back end is urged against a standard flanged connector used in the tri-clover system and held together using a standard tri-clover clamp, either a three piece or two-piece clamp, or indeed any other design of clamp used with the standard tri-clover system. As shown, the tube 3002 is rolled back over a tubing support 3010, the tubing support being provided with a lip 3014, and the lip 3014 having a step 3024. A sleeve 3020 is provided, having a rim 3028, which clips over the step 3024 in use, as described above, holding the tubing support 3010 and the sleeve 3020 together. The sleeve 3020 is in the form of a flanged connector, and thus its upper surface 3031 is in the form of a flanged connector 3036. As shown the flange 3036 is provided with a projecting ring 2037, which may be continuous or discontinuous, which can mate into a corresponding depression in a standard flanged connector 3050. This provides a means of locating the rolled end over the opening 3052 of the flanged connector. The sealing end 3006 of the rolled back end, seals against the flat surface 3054 on the front of the flanged connector. The arrangement is held together by a standard tri-clover clamp 3060 as discussed above. As is standard in tri-clover systems, the flanged connector 3050 is provided with a barbed end 3056 over which another tube 3002' fits. Thus, this arrangement provides for connection between a rolled end and the standard tri-clover system.

Figure 8:
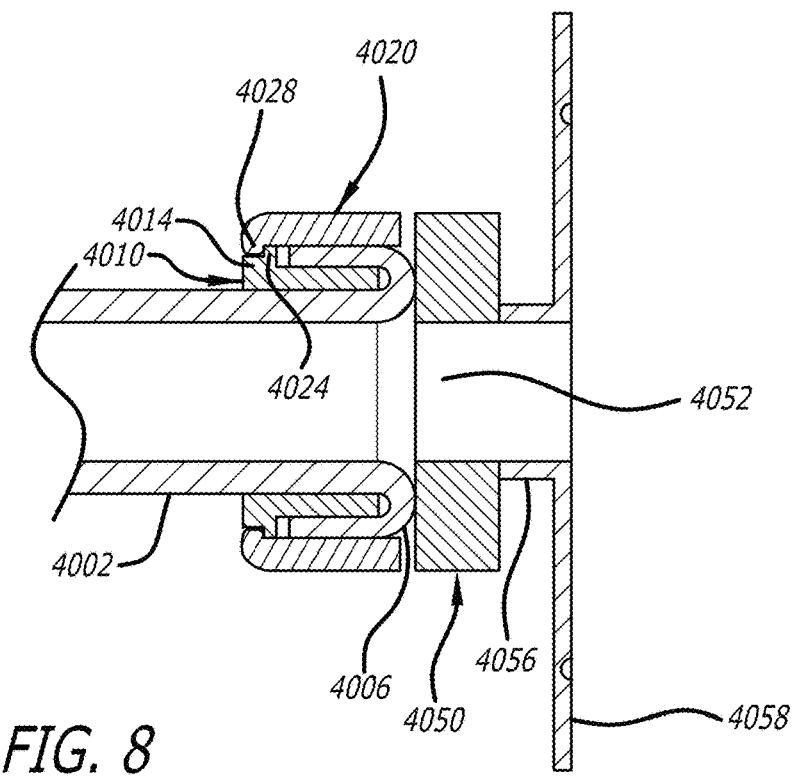
FIG. 8 is a cross-sectional view of a rolled end connected to a blank bearing a flanged connector.

Turning now to FIG. 8, this shows an alternative arrangement for connection between a rolled end tube and the standard tri-clover system. In this arrangement the rolled back end is connected to a blank, which provides a sealing surface therefor and onward connection to a flanged connector, which can be used in all standard tri-clover connections.

As shown the tube 4002 is rolled back over a tubing support 4010, the tubing support being provided with a lip 4014, and the lip 4014 having a step 4024. A sleeve 4020 is provided, having a rim 4028, which clips over the step 4024 in use, as described above, holding the tubing support 4010 and the sleeve 4020 together. The sleeve 4020 is an entirely standard sleeve as described above. The sealing surface 4006 of the rolled back end is urged against a blank end 4050 having an aperture 4052 therethrough. The blank end is sized to correspond to the size and shape of a rolled back end supported by tube support and sleeve (for example as described with reference to 4002, 4010 and 4020). This enables the rolled back end 4006 to be held in sealing arrangement with the blank end 4050 by a clamp designed to hold together two rolled back ends and described elsewhere. The blank end also comprises a tubular connector 4056 to a flanged connector 4058, the flanged connector being in accordance with standard flanged connectors of the tri-clover system. It can thus be connected to another such flanged connector in a tri-clover based system in the usual manner, i.e., using a tri-clover style clamp. This arrangement allows the rolled back end to be connected onwards to a system which used the standard tri-clover system.

Figure 9:
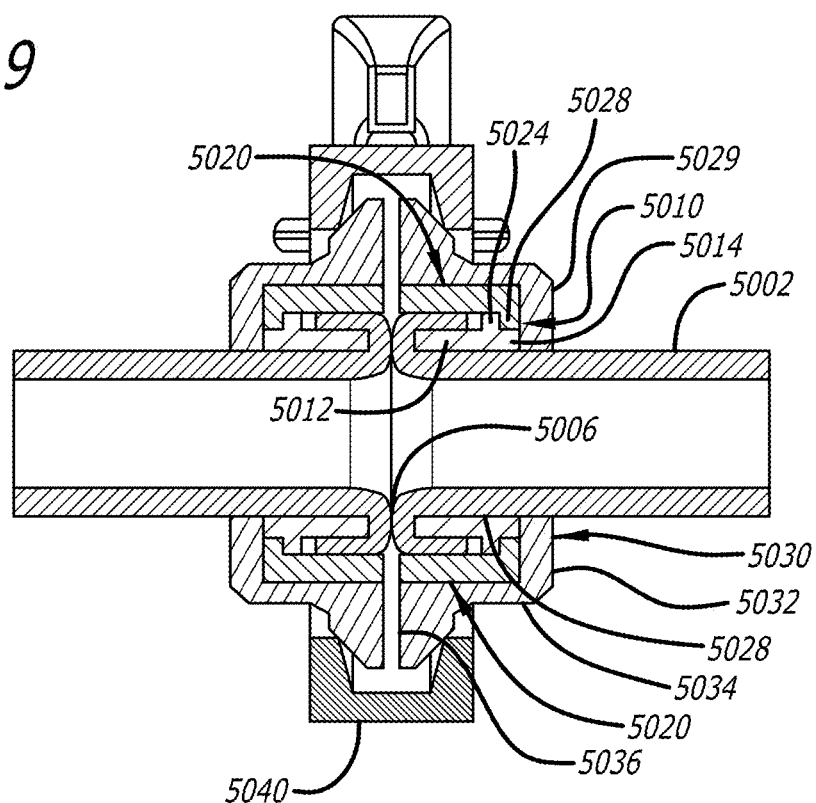
FIG. 9 is a cross-sectional view of a further alternative connection between the rolled end and a flanged connector of a tri-clover system.

As connection using tri-clover clamps in standard within the industry, the fittings surrounding rolled back ends can be adapted for use with tri-clover clamps. FIG. 9 shows a pair of rolled back ends held together with a tri-clover clamp. Each end has a tube 5002 which is supported by a tube support 5010 and sleeve 5020. A lip 5014, on the tube support 5010 having a step 5024, over which a rim 5028 from the sleeve 5020 clips, holding the elements together. The arrangement also includes a flanged connector 5030 having a catch 5032 designed to fit behind the lip 5014 of the tubing support. The connector 5030 also have a tubular section 5034 which fits over the sleeve 5020 and a flange portion 5036. The flange portion 5036 is shaped to engaged with a tri-clover clamp 5040, such that the tri-clover clamp can hold the edges of the flanges together, drawing the flanges together, urging the rolled ends against each other in sealing arrangement 5006.

Figure 10:
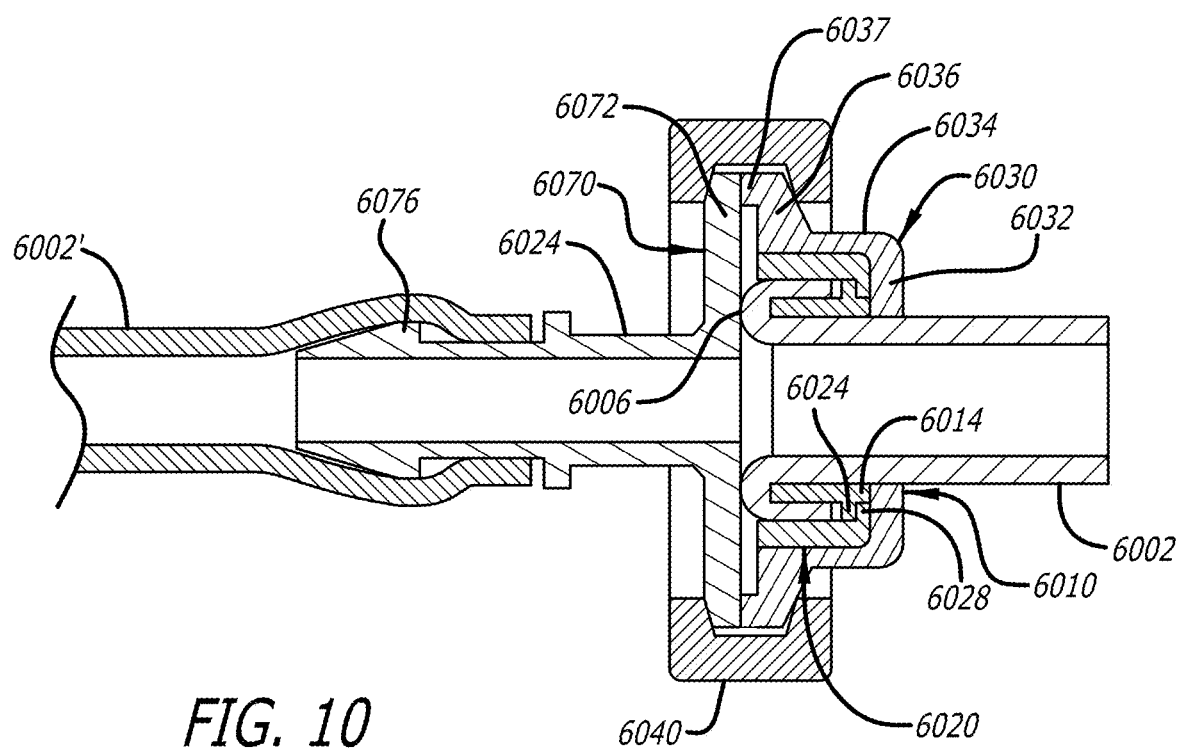
FIG. 10 is a cross-sectional view of an alternative connection between two rolled ends using a tri-clover clamping system.

FIG. 10 shows a similar arrangement to that of FIG. 10 but to allow a rolled end to seal to a flanged connector which forms part of a tri-clover system. As above, the rolled end comprises end has a tube 6002 the end of which is rolled back and supported by a tube support 6010 and sleeve 6020. A lip 6014, on the tube support 6010 having a step 6024, over which a rim 6028 from the sleeve 6020 clips, holding the elements together. The arrangement also includes a flanged connector 6030 having a catch 6032 designed to fit behind the lip 6014 of the tubing support. The connector 6030 also have a tubular section 6034 which fits over the sleeve 6020 and a flange portion 6036. The flange portion 6036 is shaped to engage with a tri-clover clamp 6040, such that attachment of the tri-clover clamp draws the flange towards another flange in the clamp. The flanged portion 6036 also include a lip 6037 for spacing from a flanged connector 6070 of a standard tri-clover arrangement. This flanged connector 6070 includes a flanged end 6072, connected to a tubular section 6074 having a barbed end 6076 over which a second tube 6002' is fitted. The design, size, and shape of the flanged connector 6030 enables the rolled end 6006 to be urged against the flanged end 6072 on the standard tri-clover system where is seals, with the tri-clover clamp holding the flanged 6030, 6070 together enabling this.

In an important feature of the invention, while the connection system can be used for connecting two tubes of the same diameter, it can also be used for connecting two tubes of different diameter. This is achieved by the use of formations, in the form of projections, bumps or expanding tapered portions to the distal end 16 of the spigot 12 of the tubing support 10, or by the use of a spigot that is thickened along its entire length.

When connecting two tubes of different sizes, usually the diameter of the smaller tube will be increased around the tubing support, for example by means of projections, bumps tapered portion or thickening of the spigot. This creates a rolled back end that has been expanded or broadened, expanding the size of the sealing or abutment surface 6. This ensures contact and sealing between the abutment surface 6 of the tube having the smaller diameter with the abutment surface 6 of the tube having the lager diameter. However, it is also possible to use similar constructions to reduce the diameter of the abutment surface on a tube with a larger diameter for connection to a tube with a smaller diameter.

Where a connection to a tube having a smaller diameter is required, a projection, bump or expanding taper 40 is provided on the inside of the spigot. Where a connection to a tube having a larger diameter is required, a projection, bump, expanding taper or thickened end 40 is provided on the outside of the spigot, or a spigot being thickened along its entire length is used.

The use of a projection, bump or taper on one spigot can be used to increase the size of the abutment surface 6 by up to ¼", but typically ¹⁄₁₆" or preferably ⅛".

The combination of two spigots, one having a projection, bump or taper 40 to connect to a tube having a larger diameter and one having a projection, bump or taper 40 to connect to a tube having a smaller diameter, can between them be used to connect tubes having a ¼" difference in their diameter, while ensuring that the abutment surfaces 6 continue to have sufficient overlap such that they can abut and form a fluid-tight seal 22. However, generally, the diameter of the roll back on a tube with a smaller diameter will generally be increased to connect to the diameter of the roll back on a tube with a larger diameter.

Figure 11:
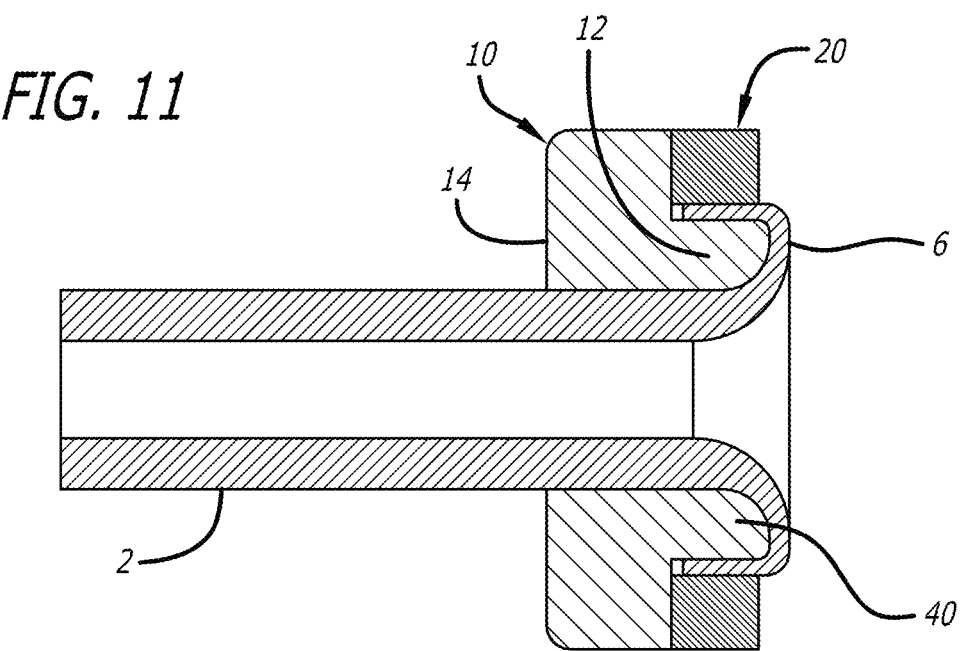
FIG. 11 is a cross-sectional view of a tube support for onward connection to a tube having a larger diameter.

FIG. 11 shows a tubing support 10 sized for used with a tube having, for example, a ¼" (6.35 mm) diameter, with the tubing support having a thickened 40 spigot 12, for connection to another tube having a diameter which is larger, for example ⅜" (9.525 mm). The extent of the expansion or contraction of the tubing that can be achieved is dependent on the flexibility of the tubing and the overlap than can be created by the thickening 40. Typically, an expansion or contraction of approximately ⅛" (3.175 mm) per tubing support can be achieved easily. However, in some cases an expansion of ¼" (6.35 mm) or ¹⁄₁₆" (1.5875 mm) is achieved. When two tubes are abutted, one can utilize a tubing support 10 designed for expansion and the other can utilize a tubing support 10 designed for contraction. As such a difference of typically ¼" (6.35 mm) can be achieved. However, in some cases a difference of ½" (12.7 mm) or ⅛" (3.175 mm) can be achieved. The presence of the projection 40 expands the size of the abutment surface 6 to ensure overlap with an abutment surface created by a tube of a larger size.

Figure 12:
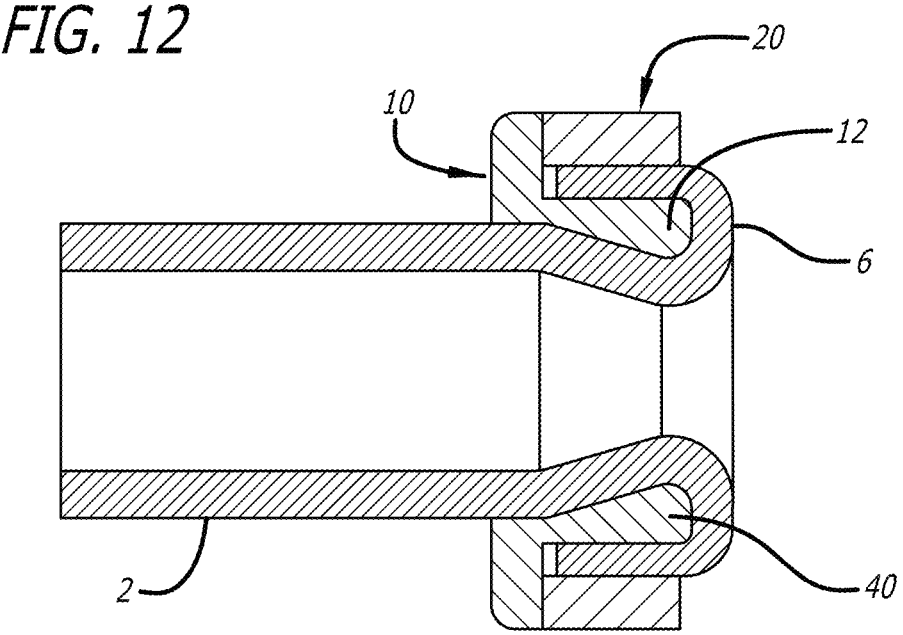
FIG. 12 is a cross-sectional view of a tube support for onward connection to a tube having a smaller diameter.

In a similar manner FIG. 12 shows a tubing support 10 sized for use with a tube having, for example, a ¾" (19.05 mm) diameter and having a tapered spigot forming a thickened end 40 for connection to another tube having a diameter which is smaller, say ⅝" (15.875 mm), the contraction again being ⅛" (3.175 mm). The projection enlarges the size of the abutment surface 6 created by the rolled back end, to ensure overlap with an abutment surface created by a tube of a smaller size.

In both FIGS. 11 and 12 connections between the support 10 and sleeve 20 are not shown, however any method of connection as discussed above may be used.

Figure 13:
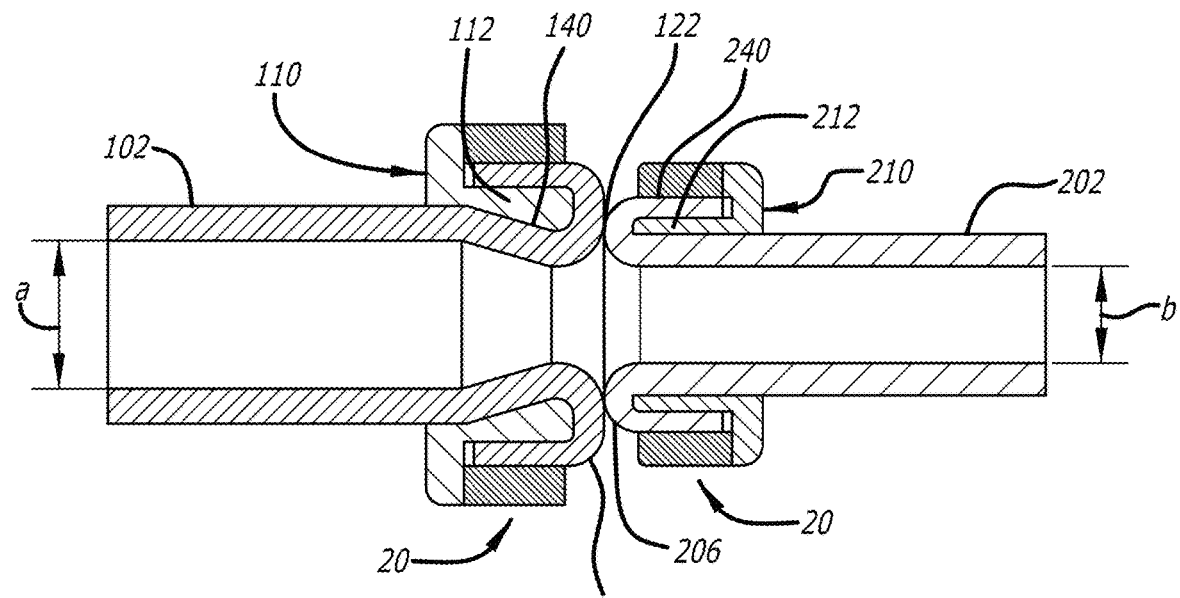
FIG. 13 is cross-sectional view of a connection between two tubes of different diameters according to the invention.

FIG. 13 shows a tube 102 having a diameter (a) of, for example ¾" (19.05 mm), connected to a tube 202 having a diameter (b) of, for example ½" (12.7 mm). Thus, the tubes have a difference in diameter of ¼" (6.35 mm) are connected using tubing supports 110, 210 similar to those described with reference to FIGS. 7 and 8 above. In this embodiment tubing support 110 is provided with tapered spigots 112. Tubing support 210 is a standard tubing support as shown in FIG. 1-3 and does not expand or contract the diameter of the tubing 202 in any way. As such FIG. 9 shows a connection between a tubing of larger diameter (a) and a tubing of smaller diameter (b) where tubing (a) is contacted in diameter, but tubing (b) is not altered in any way. Alternately, the tubing support 110 could be provided with projections or bumps its distal end and tubing support 210 could be provided with a taper extended outward from the centre of the tube, or with bumps or projections on its distal end.

The tubing support 110 supporting tube 102 is provided with a spigot 112 having a taper 140 which expands the abutment surface 106 inwardly with respect to the centre of the tube 102.

Thus, even though the tubes 102 and 202 have different diameters (a) and (b), a seal 122 can be formed between the abutment surfaces 106, 206.

As can be seen due to the increased size in the abutment surfaces 6 created by rolling back the ends of the tubes over the respective spigots 112, 212, the abutment surfaces can still create a seal 26 therebetween, even though the diameters of the tubes differ by, for example ¼" (6.35 mm).

Connections between tubing of other differing sizes can also be envisaged.

Figure 14:
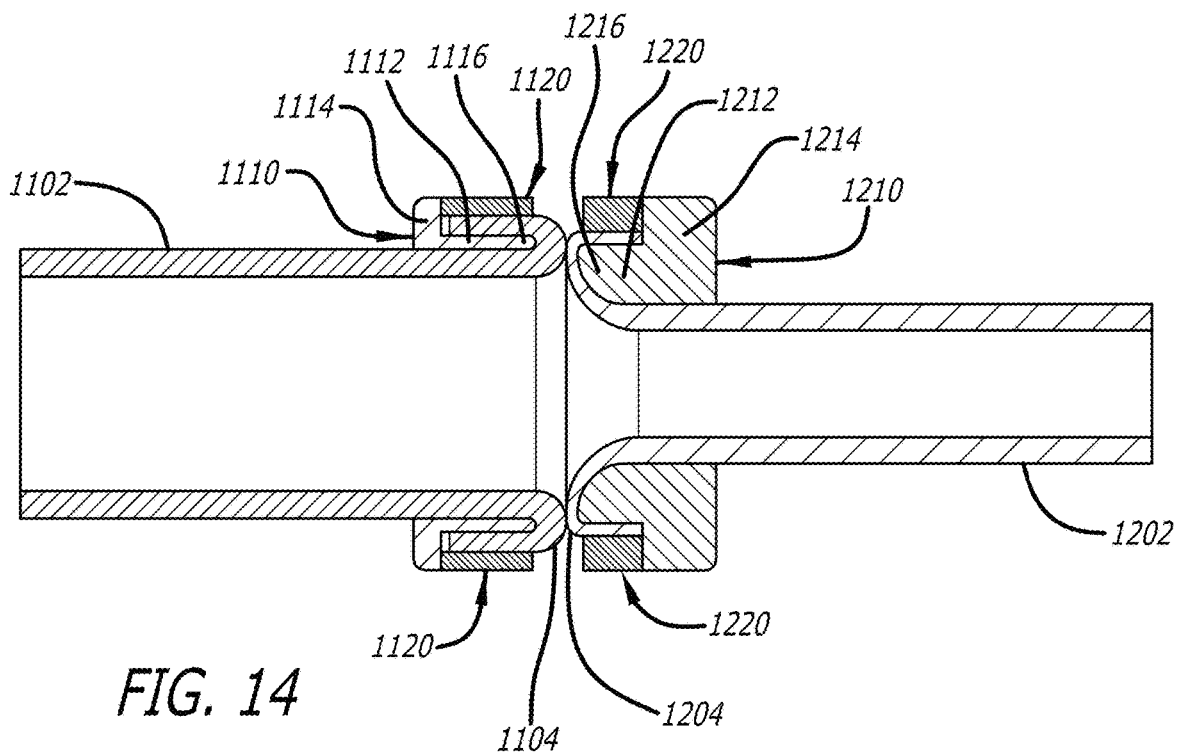
FIG. 14 is a cross-sectional view of a connection between two different tubes having different diameters according to the invention.

FIG. 14 shows a connection between a first tube 1102 having one diameter, in this example 1", and a second tube 1202 having a different diameter, in this case ½". These tubes have a different in diameter of ½", which can be accommodated using the adaptations to the tube support as described, although this is approximately the limit of the expansion that can be easily achieved.

Tube 1102 is provided with a tubing support 1110 having a standard, or indeed slightly narrow, spigot 1112 and a standard lip 1114. In contrast, tube 1202 is provided with a tubing support 1210 which is considerably thickened. In particular the spigot 1212 is thickened along its length and has a smooth curved taper towards its distal end 1216, around which tube 1202 is rolled back. The spigot 1212 is thickened sufficiently that portion of tube 1202 around its distal end 1216 abuts the portion of the first tube 1102 around distal end 1116 of its spigot 1112.

Tube 1102 is also provided with a sleeve 1120 which is of a standard size. This connects to the lip 1114 of the tubing support 1110 securing these members together.

Tube 1202 is also provided with a sleeve 1220, but this sleeve is thickened compared to standard sleeves. Correspondingly, lip 1214 is longer than standard lips. This enables abutment and connection between the sleeve 1120 and lip 1214 as previously described.

As can be see the thickening of the spigot 1210 and sleeve 1220 has two purposes. Firstly, it enables abutment between the rolled back end 1204 of a tube of a smaller diameter and the rolled back end 1104 of a tube of larger diameter, in which the tube of larger diameter is rolled back and supported using a standard sized, i.e., without thickening, tube support 1110 and sleeve 1120. Thus, the thickening of the spigot 1212 enables the rolling back of the end of tube 1202 over a wider radius, providing an abutment surface of greater diameter than if it had been rolled back directly over itself, or a spigot of a standard size. Secondly, the thickening of the spigot 1212 and the sleeve 1220 enables the outer surface of the two sleeves 1120 and 1220 to have the same diameter on abutment. This provides for ease of clamping the pairs of tubing support and sleeve together to create a seal between two tubes.

Figure 15:
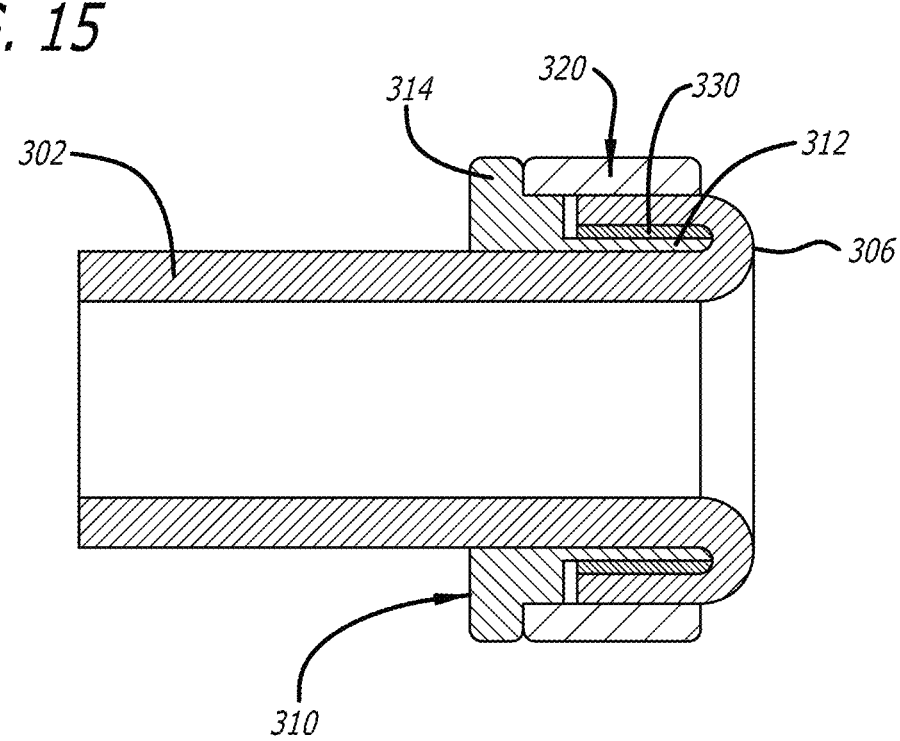
FIG. 15 is a cross-sectional view of a sealing abutment according to the invention incorporation a cushion.

As shown in FIG. 15, to aid the stability of the roll back, where the tube 302 is made from certain materials, in particular PVC, an additional cushion 330 is advantageous between the spigot 312 of the tubing support 310, and the tube 302. This has been found to provide additional stability when using such tubes.

As shown no connection is provided between the support 310 and sleeve 320. This optional element could be provided but is not necessary.

Figure 16:
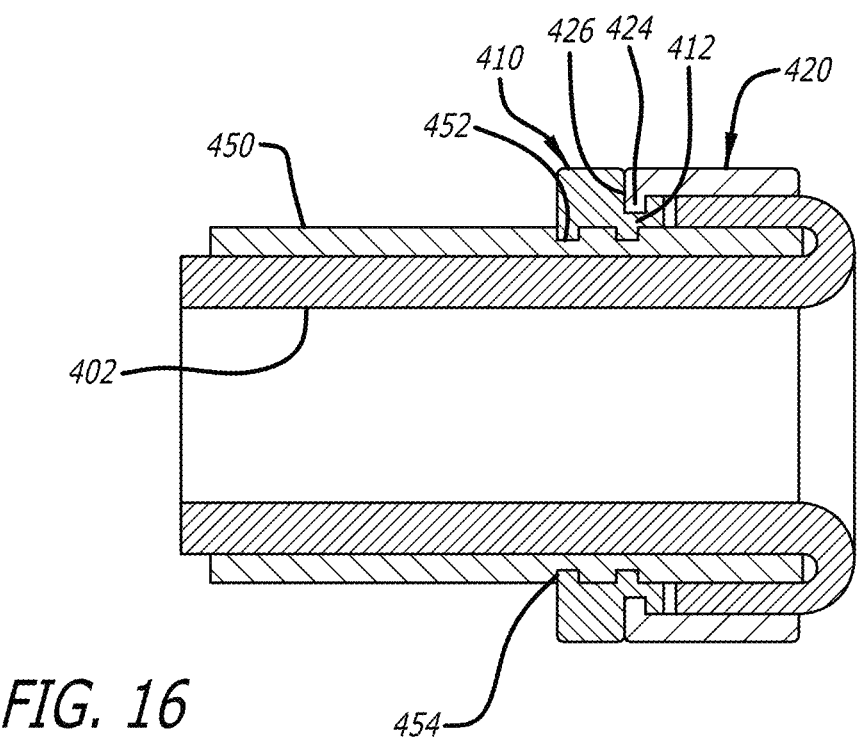
FIG. 16 is a cross sectional view of a seal abutment according to the invention formed from a flexible tube lining inside a semi-flexible or rigid tube.

Turning now to FIG. 16, the connection system using the rolled back end of a flexible tube can be utilised in systems formed from semi-flexible or rigid tubing for example made from PVC (of certain formulations). In such cases a flexible tube, 402, for example made from silicone, can be inserted inside a semi-flexible or rigid tube 450. To create a sealing surface the end of the flexible tube 402 is rolled back over itself and the semi-flexible or rigid tube. The rolled back end is supporting using a tubing support 410 very similar to those of the previous embodiments. Here the tubing support is shown with a spigot 412 of reduced length. However, a spigot of a standard length may also be used. The tubing support is provided with projections 452 which mate with channels 454 provided in the semi-flexible or rigid tube. These mating projections 452 and channels 454 act to secure the tubing support 410 in position.

As with previous embodiments a sleeve 420 holds the flexible tube 402 in its rolled back position. As shown the sleeve 420 is secured to the tubing support 410 by a projection 426 on the sleeve mating into a groove 424 in the tubing support. This connection between the support 410 and sleeve 420 is not necessary. It provided added security between the elements and also provided a "click" fit providing the user with reassurance that the device has been correctly fitted. However, this connection is not necessary and, in many embodiments, will not be provided.

As in previous embodiments the rolled back end of the flexible tube 402 creates a sealing surface 406 which can be abutted against another sealing surface creating a sealed joint. One advantage of this system is that it enables the semi-flexible or rigid tube to be made from a lower grade of material, as the fluid will be passing through the silicone tubing, supported inside the semi-flexible or rigid tube.

Figure 17:
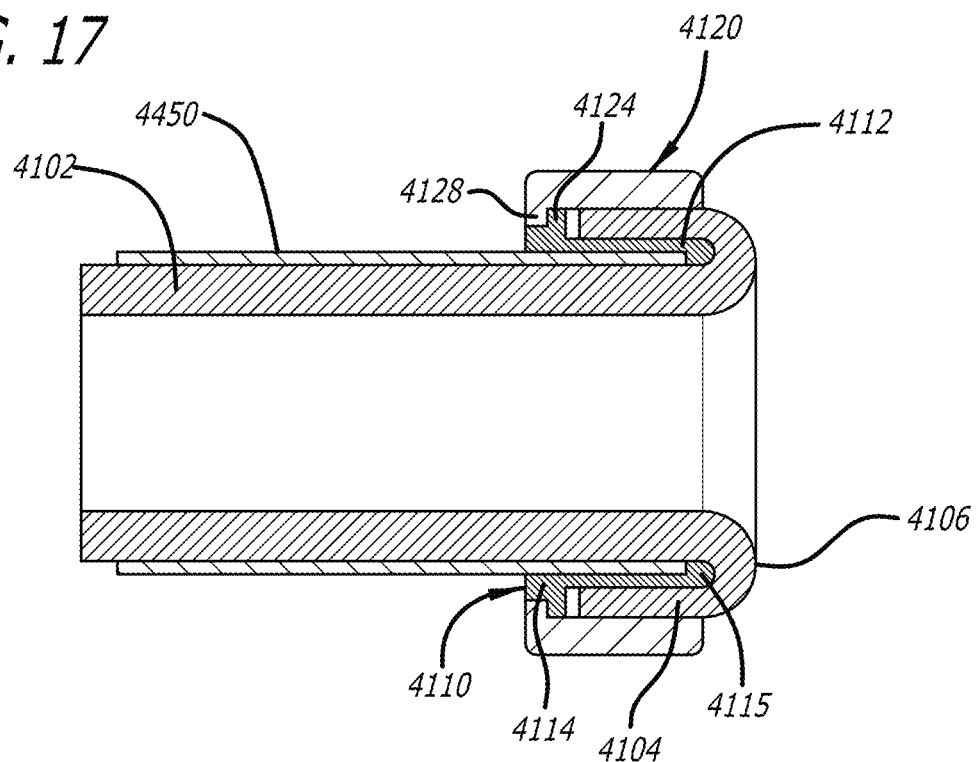
FIG. 17 is a cross-sectional view of an alternative sealing abutment according to the invention formed from a flexible tube lining a semi-flexible or rigid tube.

FIG. 17 shows a further alternative arrangement for the connection system using the rolled back end of a flexible tube in systems formed from semi-flexible or rigid tubing. As in the embodiment shown in FIG. 12, a flexible tube, 4102, is inserted inside a semi-flexible or rigid tube 450. To create a sealing surface the end of the flexible tube 402 is rolled back over itself and the semi-flexible or rigid tube.

The rolled back end 4104 is supporting using a tubing support 4110 having many similarities to those of the previous embodiments. Here the tubing support is shown with a spigot 412, having an inwards projection 4115 which forms and abutment for the end of the semi-flexible or rigid tube 4150.

In this embodiment no projections are provided on the underside of the spigot, as present in the embodiment of FIG. 16, and no corresponding grooves are provided in the semi-flexible or rigid tube. While such projections and grooves can be provided, they are generally not essential.

As with previous embodiments a sleeve 4120 holds the flexible tube 4102 in its rolled back position. As shown the sleeve 4120 is secured to the tubing support 4110 by sleeve 4120 having a rim 4128 which clips over a step 4124 provided on the lip 4114 on the tubing support 4110. This is as described in the embodiment of FIG. 1. However, other methods of connecting the sleeve 4120 and the tubing support 4110 as described in other embodiments, could also be used.

As in previous embodiments the rolled back end of the flexible tube 4102 creates a sealing surface 4106 which can be abutted against another sealing surface creating a sealed joint. One advantage of this system is that it enables the semi-flexible or rigid tube to be made from a lower grade of material, as the fluid will be passing through the silicone tubing, supported inside the semi-flexible or rigid tube.

Figure 18:
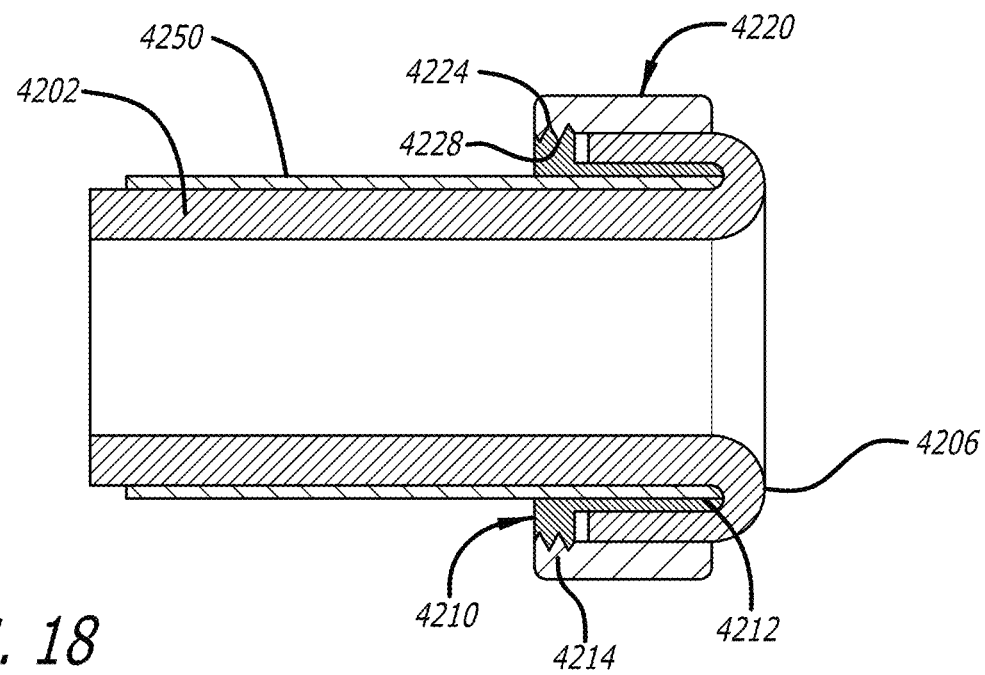
FIG. 18 is a cross-sectional view of a further alternative sealing abutment according to the invention formed from a flexible tube lining a semi-flexible or rigid tube.

Turning now to FIG. 18, this shows a further embodiment in which the connection system using the rolled back end of a flexible tube is utilised in systems formed from semi-flexible or rigid tubing.

This embodiment is very similar to that of FIG. 17, with the exception that the tubing support is not provided with an inwards projection and thus does not incorporate an abutment for the semi-flexible or rigid tube.

As shown a flexible tube, 4202, for example made from silicone, has been inserted inside a semi-flexible or rigid tube 4250. To create a sealing surface the end of the flexible tube 4202 is rolled back over itself and the semi-flexible or rigid tube. The rolled back end is supporting using a tubing support 4210 very similar to those of the previous embodiments, having a spigot 4212 and a lip 4214. The flexible tube 4202 is rolled back over the semi-flexible or rigid tube 4250 and the tubing support 4210.

As with previous embodiments a sleeve 4220 holds the flexible tube 4202 in its rolled back position. As shown the sleeve 4220 is secured to the tubing support 4210 by mating screw threads; a screw thread 4224 on the sleeve 4220 and a mating screw thread 4228 on the lip of the tubing support 4210.

As in previous embodiments the rolled back end of the flexible tube 4202 creates a sealing surface 4206 which can be abutted against another sealing surface creating a sealed joint.

As noted, the apparatus and method of the present invention can be used in building a bio-disposable system, for example for batch production, semi-permanent production, experimental or testing systems.

Such systems typically include a valve, and such a valve can be provided using the apparatus of the invention.

The semi-flexible to rigid tubing of FIGS. 16-18 may be made from PVC, for example of certain formulations having insufficient flexibility and elasticity to form a seal, from plastic tubing having internal braiding, or even metallic tubing.

Figure 19:
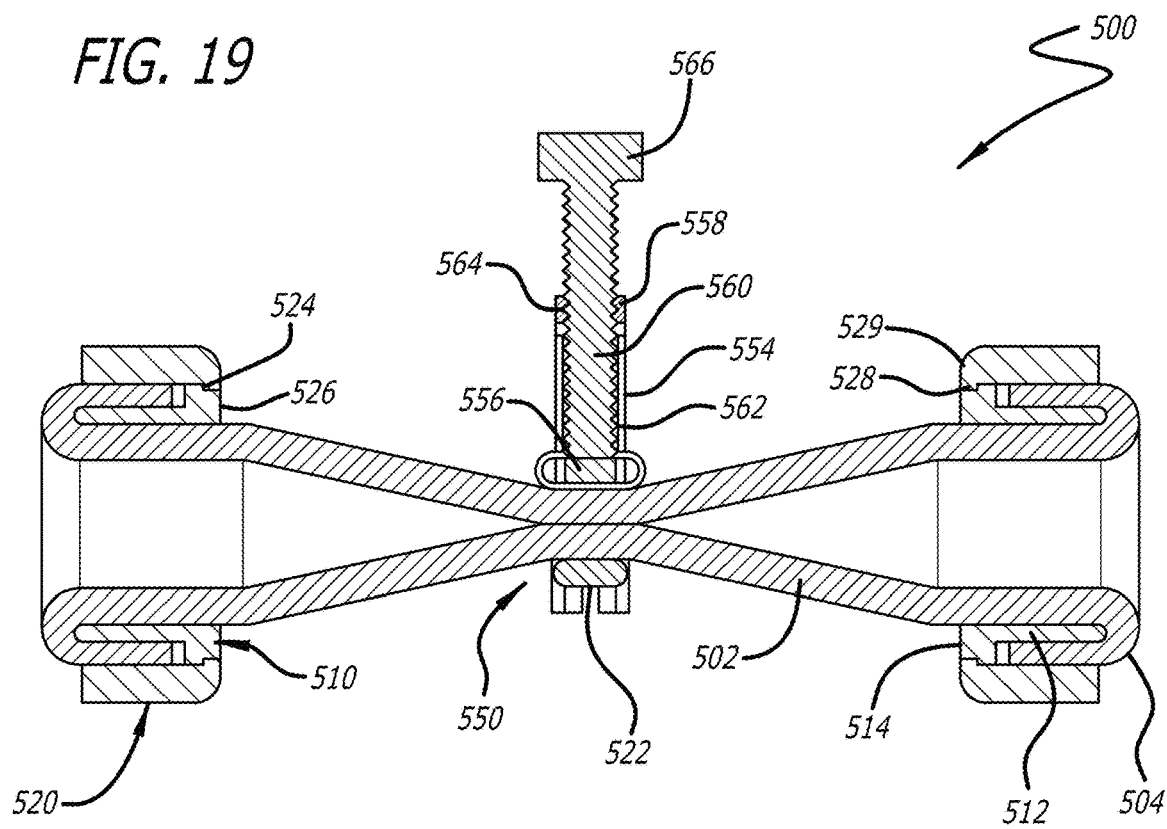
FIG. 19 is a cross-sectional view of a valve using a length of tube having the rolled back ends of the invention.

FIG. 19 shows a valve using the apparatus as described above. The valve 500 comprises a length of tubing 502, each end 504 of which has been rolled back using the apparatus described above. Thus, each end 504 of the tube has been rolled back over a tubing support 510, which comprises a spigot 512 and a lip 514. Each rolled back end 504 is supported by a sleeve 520.

The connection between the tubing support 510 and sleeve 520 is as described with reference to FIG. 1. As shown, the lip 514 of the tubing support 10 is provided with a downwards step 524 adjacent is back edge 526. The sleeve 520 is provided with a projecting rim 528 adjacent is end 529. When the tubing support 510 is positioned over the tube 502, the end of the tube is rolled back over the tubing support 510 and the sleeve 520 is positioned over the rolled back end 504, the rim 528 of the sleeve clips over the step 524 of the lip 514 securing the sleeve 520 in position.

Provided between the rolled back ends 504 of the tube 502 is a clamp 550. The clamp can be any type of clamp that is capable of compressing the tube so that there can be no flow long the tube 502, and of incrementally restricting the flow along the tube.

As shown the clamp is provided with a seat 552 on which the tube 502 sits, two upright members 554 extending from either end of the seat 552, and a compression member 556, able to move up and down the upright members 554 to which it is connected. The clamp also includes a top member 558 fixedly connected to the tops of the upright members 554. Finally, the clamp includes a screw member 560 joined to the compression member 556. The screw member 560 comprises a screw thread 562 along its length, which mates with a screw thread in an aperture 564 in the top member 558, and a handle 566 for rotation of the screw member 560.

The tube 502 is positioned on the seat 552 and between the upright members 554 and compression member 556. On rotation of the handle 566, the compression member 556 is moved down along the upright members 554 towards the seat. As it moves it restricts the internal volume of the tube 502, restricting the flow. On continued turning of the handle, the restriction member 556 compresses the tube 502 against the seat 552, urging opposite sides of the tube against each other, and completely preventing any flow along the tube. As the tube 502 is a flexible tube, it will conform to the shape of the seat and compression member, which are designed to enable complete compression of the tube. Equally, on turning of the handle the other way, the compression member is lifted away from the seat, allowing flow through the tube. Such clamps are well known, and other types of clamp could also be used.

Figure 20:
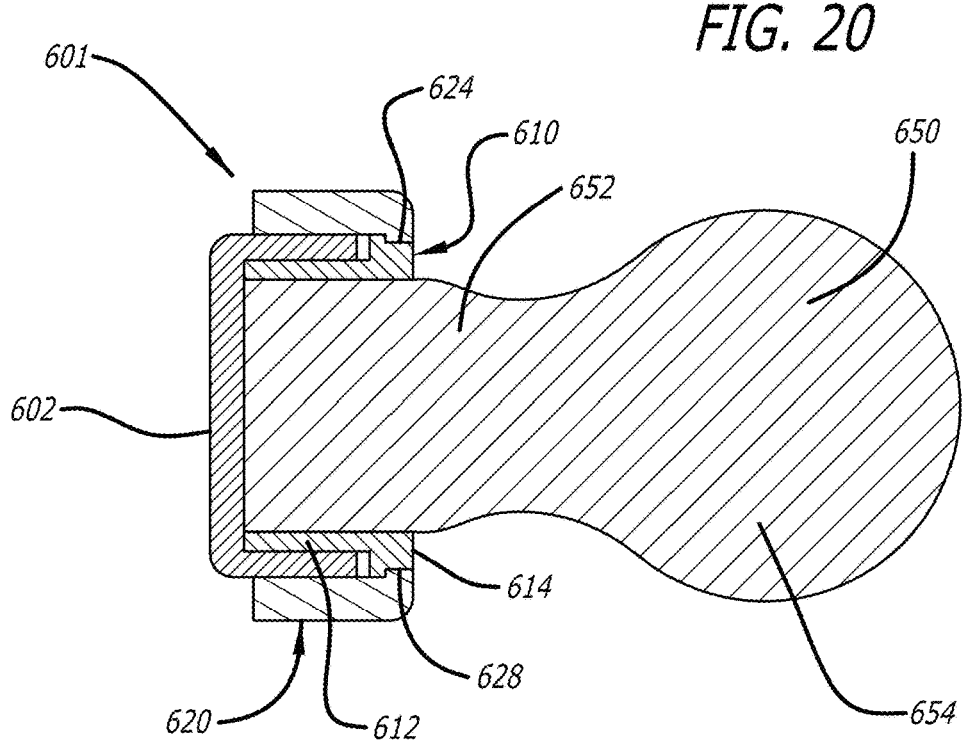
FIG. 20 is a cross-sectional view of an end cap using the rolled back end of the invention.

In addition, bio-disposable systems often require an end cap, and this can also be provided using the apparatus of the invention. As shown in FIG. 20, the end cap 601 there shown utilizes the tubing support 610 and sleeve 620 system described in previous embodiments. This allows for connection between two rolled back ends, or two sets of supports supporting the rolled back ends.

As shown the end cap 601 comprises a tubing support 610 and a sleeve 620 holding a sheet of flexible material 602. Thus, the sheet 602 is held between the tubing support and the sleeve 620 as previously described. This enables the support/sleeve combination to be connected to another support/sleeve combination as described above. In addition, this arrangement also provides a closed, sealing end 606.

Within the tubing support 610 is provided a bung 650. This bung 650 may be separate from the tubing support 610, but sized for an interference fit therein, providing a closed structure. Alternatively, the bug 650 can be moulded into the tubing support 610 on manufacture. The bung 650 includes an end 652 sized to fit within the tubing support 610, and another end 654 shaped as a handle. The handle can used to position the bung (where provided separately from the tubing support 610, and to manipulate the end cap 601 as a whole.

While the shape of the bung 650 is shown as shaped for finger hold, including a fitting end 652 and a handle end 655, the shape of the handle end 655 may vary. For example, the handle may be an extension of the fitting end 565, with parallel sides.

Such an end cap can be used to seal off an end of a tube or connection.

Such connections between tubes can be used in many situations. The ability to seal a tube by abutting a sealing further created by its end reduces the number of materials that any fluid passing through the tube must contact, reducing the risk of contamination, and also reducing non-flow areas in which reduce the flow efficiency of the tube and in which contaminants can collect.

The invention claimed is:
1. Apparatus for forming an external sealing end from a length of a flexible tubing, the apparatus comprising
   a tubing support, the tubing support comprising an annular spigot and a tube opening having an internal diam- eter, the annular spigot having a smooth inner surface, an outer surface, and a lip; and a sleeve, the sleeve being annular in shape and comprising a support opening having an internal diameter, the sleeve having a smooth inner surface and a smooth outer surface and a length that is less than or equal to the length of the tubing support;

wherein the internal diameter of the tube opening of the tubing support is sized to receive therethrough the flexible tubing;

wherein the spigot is sized to receive an end of the flexible tubing rolled back onto the outer surface, thereby forming the external sealing end of the flexible tubing;

wherein the lip is located on the outer surface of the spigot and extends substantially perpendicularly to the spigot, the lip providing a stop for the sleeve and the end of the flexible tubing rolled back onto the outer surface of the spigot;

wherein the lip is provided with a channel and the sleeve is provided with one or more projections sized to mate into the channel on correct positioning of the tubing support and sleeve, connecting them together, or, wherein the lip is provided with one or more projections, and the sleeve is provided with a channel sized to mate over the projections on correcting positioning of the tubing support and sleeve, connecting them together;

wherein the internal diameter of the support opening of the sleeve is sized to fit over the end of the flexible tubing rolled back onto the outer surface of the spigot and the tubing support; and wherein the tubing support and the sleeve are sized to be directly fixably engaged with each other.

2. Apparatus as claimed in claim 1, wherein the spigot is sized to receive the end of the flexible tubing rolled back onto the outer surface as a location fit or as a loose fit.

3. Apparatus as claimed in claim 1, wherein the internal diameter of the support opening of the sleeve is sized to form an interference fit over the end of the flexible tubing rolled back onto the outer surface of the spigot and the tubing support.

4. Apparatus as claimed in claim 1, wherein the sleeve further includes a lip located on the inner surface and extending substantially perpendicularly to the sleeve.

5. Apparatus as claimed in claim 1, wherein both the tubing support and the sleeve are provided with lips extending substantially perpendicularly to the spigot and sleeve, and towards each other in use.

6. Apparatus as claimed in claim 5, wherein the tubing support lip is provided with a step, and the sleeve lip is in the form of a rim, the step and the rim enabling the connection between the tubing support and sleeve.

7. Apparatus as claimed in claim 1, wherein the lip is provided with a channel and the sleeve is provided with one or more projections sized to mate into the channel on correct positioning of the tubing support and sleeve, connecting them together.

8. Apparatus as claimed in claim 1, wherein the lip is provided with one or more projections, and the sleeve is provided with a channel sized to mate over the projections on correcting positioning of the tubing support and sleeve, connecting them together.

9. Apparatus as claimed in claim 1, wherein the spigot is provided with a distal end adapted to abut to a flexible tubing having a smaller diameter.

10. Apparatus as claimed in claim 1, wherein the spigot is provided with a distal end adapted to abut to a flexible tubing having a larger diameter.

11. Apparatus as claimed in claim 10, wherein the spigot is thickened along its length, providing a greater radius over which the flexible tubing can be rolled back.

12. Apparatus as claimed in claim 11, wherein the thickened spigot is tapered and rounded.

13. Apparatus as claimed in claim 1, wherein the sleeve forms a flanged connector.

14. Apparatus as claimed in claim 1, wherein the sleeve forms an abutment connector, having a flanged end.

15. A method of forming an external sealing end from a length of a flexible tubing, the method comprising:

pushing a tubing support of the apparatus according to claim 1 over an end of the flexible tubing such that a lip of the tubing support is furthest from the end of the flexible tubing and the spigot is positioned a short distance from the end of the flexible tubing;

rolling the end of the flexible tubing back over the outer surface of the spigot to form the external sealing end, the length of rolled back tube not extending past the lip or end of the spigot;

pushing a sleeve of the apparatus according to claim 1 over the length of the rolled back tube and directly fixably engaging the sleeve to the tubing support in a manner that maintains the external sealing end.

16. A method of connecting a first flexible tubing to a second flexible tubing, the method comprising:

forming a first external sealing end from a length of the first flexible tubing using a first apparatus comprising a first tubing support and a first sleeve according to claim 15;

forming a second external sealing end from a length of the second flexible tubing using a second apparatus comprising a second tubing support and a second sleeve according to claim 15; and urging the first external sealing end and the second sealing end into direct contact against each other to create the fluid tight connection.

17. A method as claimed in claim 16, wherein the first and second external sealing ends are clamped together using a clamping system.

18. Apparatus as claimed in claim 1, wherein the annular spigot has an outer surface that is smooth or has an outer surface containing protrusions, projections or barbs to assist in holding the end of the flexible tubing rolled back in position on the outer surface of the spigot.

* * * * *